(12) United States Patent
Mueller et al.

(10) Patent No.: US 8,958,883 B2
(45) Date of Patent: Feb. 17, 2015

(54) ELECTRICAL STIMULATION DEVICE AND METHOD FOR THERAPEUTIC TREATMENT AND PAIN MANAGEMENT

(76) Inventors: Pierre-Yves Mueller, Collonge-Bellerive (CH); Marshall Masko, St. Louis Park, MN (US); Pierre-Yves Lampo, Morrens (CH); Klaus Schonenberger, Vufflens-La-Ville (CH); Felix Buhlmann, Lausanne (CH); Steve Guex, Givrins (CH); Gary L. Moore, Cedar, MN (US); Patrick Lavalley, Elk River, MN (US)

( * ) Notice: Subject to any disclaimer, the term of this patent is extended or adjusted under 35 U.S.C. 154(b) by 1747 days.

(21) Appl. No.: 11/918,761
(22) PCT Filed: Apr. 19, 2006
(86) PCT No.: PCT/US2006/014734
§ 371 (c)(1),
(2), (4) Date: Nov. 5, 2009
(87) PCT Pub. No.: WO2006/113801
PCT Pub. Date: Oct. 26, 2006

(65) Prior Publication Data
US 2010/0042180 A1    Feb. 18, 2010

Related U.S. Application Data

(60) Provisional application No. 60/672,937, filed on Apr. 19, 2005.

(51) Int. Cl.
*A61N 1/372* (2006.01)
*A61N 1/36* (2006.01)
(Continued)

(52) U.S. Cl.
CPC .......... *A61N 1/36021* (2013.01); *A61N 1/0456* (2013.01); *A61N 1/322* (2013.01); *A61N 1/3756* (2013.01)
USPC .......................................................... 607/46

(58) Field of Classification Search
USPC .......................................................... 607/46
See application file for complete search history.

(56) References Cited

U.S. PATENT DOCUMENTS 2,263,205 A    11/1941    Conrad
3,344,792 A    10/1967    Offner at al.
(Continued)

FOREIGN PATENT DOCUMENTS

DE    3216911    11/1983
DE    19545238    5/1997
(Continued)

OTHER PUBLICATIONS

Strojnik et al., "Chapter 78 Implantable Stimulators for neuromuscular control," The Biomedical engineering handbook, Second Edition, vol. 1, Editor: Joseph D. Bronzino, CRC Press, IEEE Press.
(Continued)

*Primary Examiner* — Joseph Dietrich
(74) *Attorney, Agent, or Firm* — Knobbe Martens Olson & Bear LLP

(57) ABSTRACT

A disposable electrical stimulation device and method for providing therapeutic treatment and pain management in a convenient, compact configuration. Electrode size and shape and relative configuration can be varied according to an intended application and use, or a universal configuration can be provided for use on almost any area of the body. The common structure of communicatively coupled dual electrodes including control circuitry and a power source accommodates a range of different sizes, configurations, stimulation treatment intensities, and other physical and electrical characteristics that can be pre-customized and packaged for specific, limited time use. The device can therefore be used in methods of providing therapy, managing pain, and achieving other treatment goals by electrical stimulation.

31 Claims, 17 Drawing Sheets

(51) Int. Cl.
  *A61N 1/04* (2006.01)
  *A61N 1/32* (2006.01)
  *A61N 1/375* (2006.01)

(56) References Cited

U.S. PATENT DOCUMENTS

| | | | |
|---|---|---|---|
| 3,628,538 A | 12/1971 | Vincent et al. |
| 3,810,457 A | 5/1974 | Bottcher et al. |
| 3,895,639 A | 7/1975 | Rodler |
| 3,918,459 A | 11/1975 | Horn |
| 4,019,518 A | 4/1977 | Maurer et al. |
| 4,068,669 A | 1/1978 | Niemi |
| 4,088,141 A | 5/1978 | Niemi |
| 4,164,740 A | 8/1979 | Constant |
| 4,165,750 A | 8/1979 | Aleev et al. |
| 4,177,819 A | 12/1979 | Kofsky et al. |
| 4,256,116 A | 3/1981 | Meretsky et al. |
| 4,324,253 A | 4/1982 | Greene et al. |
| 4,342,317 A | 8/1982 | Axelgaard |
| 4,363,324 A | 12/1982 | Kusserow et al. |
| 4,372,319 A | 2/1983 | Ichinomiya et al. |
| 4,390,023 A | 6/1983 | Rise |
| 4,392,496 A | 7/1983 | Stanton |
| 4,408,609 A | 10/1983 | Axelgaard |
| 4,503,863 A | 3/1985 | Katims |
| 4,535,777 A | 8/1985 | Castel |
| 4,569,352 A | 2/1986 | Petrofsky et al. |
| 4,580,339 A | 4/1986 | Ioffe |
| 4,582,063 A | 4/1986 | Mickiewicz et al. |
| 4,586,495 A | 5/1986 | Petrofsky |
| 4,614,178 A | 9/1986 | Harlt et al. |
| 4,632,117 A | 12/1986 | James |
| 4,640,286 A | 2/1987 | Thomson |
| 4,664,118 A | 5/1987 | Batters |
| 4,669,477 A | 6/1987 | Ober |
| 4,690,145 A | 9/1987 | King-Smith et al. |
| 4,706,674 A | 11/1987 | Dieken et al. |
| 4,769,881 A | 9/1988 | Pedigo et al. |
| 4,785,813 A | 11/1988 | Petrofsky |
| 4,803,988 A | 2/1989 | Thomson |
| 4,805,636 A | 2/1989 | Barry et al. |
| 4,811,742 A | 3/1989 | Hassel et al. |
| 4,848,347 A | 7/1989 | Hall |
| 4,887,603 A | 12/1989 | Morawetz et al. |
| 4,919,139 A | 4/1990 | Brodard |
| 4,926,865 A | 5/1990 | Oman |
| 4,976,264 A | 12/1990 | Petrofsky |
| 4,977,895 A | 12/1990 | Tannenbaum |
| 4,996,987 A | 3/1991 | Petrofsky |
| 5,041,974 A | 8/1991 | Walker et al. |
| 5,048,522 A | 9/1991 | Petrofsky |
| 5,067,478 A | 11/1991 | Berlant |
| 5,067,495 A | 11/1991 | Brehm |
| 5,070,873 A | 12/1991 | Graupe et al. |
| 5,081,989 A | 1/1992 | Graupe et al. |
| 5,092,329 A | 3/1992 | Graupe et al. |
| 5,113,176 A | 5/1992 | Harris |
| 5,117,826 A | 6/1992 | Bartelt et al. |
| 5,123,413 A | 6/1992 | Hasegawa et al. |
| 5,131,401 A | 7/1992 | Westenskow et al. |
| 5,161,530 A | 11/1992 | Gamble |
| 5,178,156 A | 1/1993 | Takishima et al. |
| 5,184,617 A | 2/1993 | Harris et al. |
| 5,233,987 A | 8/1993 | Fabian et al. |
| 5,285,781 A | 2/1994 | Brodard |
| 5,300,096 A | 4/1994 | Hall et al. |
| 5,350,414 A | 9/1994 | Kolen |
| 5,397,338 A | 3/1995 | Grey et al. |
| 5,413,550 A | 5/1995 | Castel |
| 5,507,788 A | 4/1996 | Lieber |
| 5,512,057 A | 4/1996 | Reiss et al. |
| 5,514,165 A | 5/1996 | Malaugh et al. |
| 5,540,235 A | 7/1996 | Wilson |
| 5,540,735 A | 7/1996 | Wingrove |
| 5,562,718 A | 10/1996 | Palermo |
| 5,653,739 A | 8/1997 | Maurer et al. |
| 5,732,401 A | 3/1998 | Conway |
| 5,748,845 A | 5/1998 | Labun et al. |
| 5,755,745 A | 5/1998 | McGraw et al. |
| 5,775,331 A | 7/1998 | Raymond et al. |
| 5,776,171 A | 7/1998 | Peckham et al. |
| 5,776,173 A | 7/1998 | Madsen, Jr. et al. |
| 5,782,893 A | 7/1998 | Dennis, III |
| 5,800,458 A | 9/1998 | Wingrove |
| 5,817,138 A | 10/1998 | Suzuki |
| 5,836,995 A | 11/1998 | MGraw et al. |
| RE35,987 E | 12/1998 | Harris et al. |
| 5,873,900 A | 2/1999 | Maurer et al. |
| 5,954,758 A | 9/1999 | Peckham et al. |
| 5,961,542 A | 10/1999 | Agarwala |
| 5,967,975 A | 10/1999 | Ridgeway |
| 5,980,435 A | 11/1999 | Joutras et al. |
| 6,026,328 A | 2/2000 | Peckham et al. |
| 6,029,090 A | 2/2000 | Herbst |
| 6,041,259 A | 3/2000 | Agarwala et al. |
| 6,044,303 A | 3/2000 | Agarwala et al. |
| RE36,690 E | 5/2000 | McGraw et al. |
| 6,064,911 A | 5/2000 | Wingrove |
| 6,086,525 A | 7/2000 | Davey et al. |
| 6,113,552 A | 9/2000 | Shimazu et al. |
| 6,146,335 A | 11/2000 | Gozani |
| 6,233,472 B1 | 5/2001 | Bennett et al. |
| 6,285,906 B1 | 9/2001 | Ben-Haim et al. |
| 6,292,692 B1 | 9/2001 | Skelton et al. |
| 6,324,432 B1 | 11/2001 | Rigaux et al. |
| 6,393,328 B1 | 5/2002 | McGraw et al. |
| 6,432,074 B1 | 8/2002 | Ager et al. |
| 6,445,955 B1 | 9/2002 | Michelson et al. |
| 6,560,487 B1 | 5/2003 | McGraw et al. |
| 6,564,103 B2 | 5/2003 | Fischer et al. |
| 6,584,358 B2 | 6/2003 | Carter et al. |
| 6,609,031 B1 | 8/2003 | Law et al. |
| 6,612,984 B1 | 9/2003 | Kerr, II |
| 6,628,492 B2 | 9/2003 | Akiyama et al. |
| 6,647,290 B2 | 11/2003 | Wuthrich |
| 6,662,051 B1 | 12/2003 | Eraker et al. |
| 6,675,048 B2 | 1/2004 | McGraw et al. |
| 6,684,106 B2 | 1/2004 | Herbst |
| 6,701,189 B2 | 3/2004 | Fang et al. |
| 6,727,814 B2 | 4/2004 | Saltzstein et al. |
| 6,826,429 B2 | 11/2004 | Johnson et al. |
| 6,839,594 B2 | 1/2005 | Cohen et al. |
| 6,845,271 B2 | 1/2005 | Fang et al. |
| 6,876,883 B2 | 4/2005 | Hurtado |
| 6,907,295 B2 | 6/2005 | Gross et al. |
| 6,963,773 B2 | 11/2005 | Waltman et al. |
| 6,988,005 B2 | 1/2006 | McGraw et al. |
| 2001/0051787 A1 | 12/2001 | Haller et al. |
| 2002/0165590 A1 | 11/2002 | Crowe et al. |
| 2003/0036683 A1 | 2/2003 | Kehr et al. |
| 2003/0065370 A1* | 4/2003 | Lebel et al. ............ 607/60 |
| 2003/0074037 A1 | 4/2003 | Moore et al. |
| 2003/0120323 A1* | 6/2003 | Meadows et al. ............ 607/46 |
| 2004/0010291 A1 | 1/2004 | Wagner et al. |
| 2004/0147975 A1 | 7/2004 | Popovic et al. |
| 2004/0167585 A1 | 8/2004 | Kovak et al. |
| 2005/0055054 A1 | 3/2005 | Yu |

FOREIGN PATENT DOCUMENTS

| | | |
|---|---|---|
| DE | 4092175 | 7/1997 |
| EP | 0269844 | 6/1988 |
| EP | 0367338 | 5/1990 |
| EP | 0706806 | 4/1996 |
| EP | 1 095 670 | 5/2001 |
| FR | 2425865 | 12/1979 |
| FR | 2504807 | 11/1982 |
| JP | 2004081676 | 3/2004 |

(56) References Cited

FOREIGN PATENT DOCUMENTS

| WO | WO-8200414 | 2/1982 |
|---|---|---|
| WO | WO-8602567 | 5/1986 |
| WO | WO-9510323 | 4/1995 |
| WO | WO-9919019 | 4/1999 |
| WO | WO-9941682 | 8/1999 |
| WO | WO-0001055 | 1/2000 |
| WO | WO-0036900 | 6/2000 |
| WO | WO-01/03768 | 1/2001 |
| WO | WO 01/51122 | 7/2001 |
| WO | WO-02085452 | 10/2002 |
| WO | WO-03008038 | 1/2003 |
| WO | WO-2004011087 | 2/2004 |
| WO | WO-2004012807 | 2/2004 |
| WO | WO-2004/018038 | 3/2004 |
| WO | WO-2004064915 | 8/2004 |

OTHER PUBLICATIONS

"*Cyclotec Pain Control Products*," Cyclotec AMT, 3 pages. Retrieved from http://www.cyclotecamt.com/pages2/products.htm on May 25, 2004.

"*Muscle Stimulator and TENS: Very different modalities*,"RS Medical, 1 page. Retrieved from http://www.rsmedical.com/products/diff/body.htm on Apr. 27, 2004.

"*Netwave*,"Blue Sky Labs; 6 pages; Copyright 2003.

"*RS-4i Sequential Stimulator*,"6 pages; Retrieved from http://www.rsmedical.com/products/rs2/body.htm on Apr. 27, 2004.

"501(k) *Summary for netwave Interferential Stimulator*,"Ryan Telemedicine, LLC; Jun. 12, 2003.

Ilic et al., "*A Programmable Electronic Stimulator for FES Systems*," IEE Transactions on Rehabilitation Engineering, vol. 2, No. 4, Dec. 1994.

\* cited by examiner

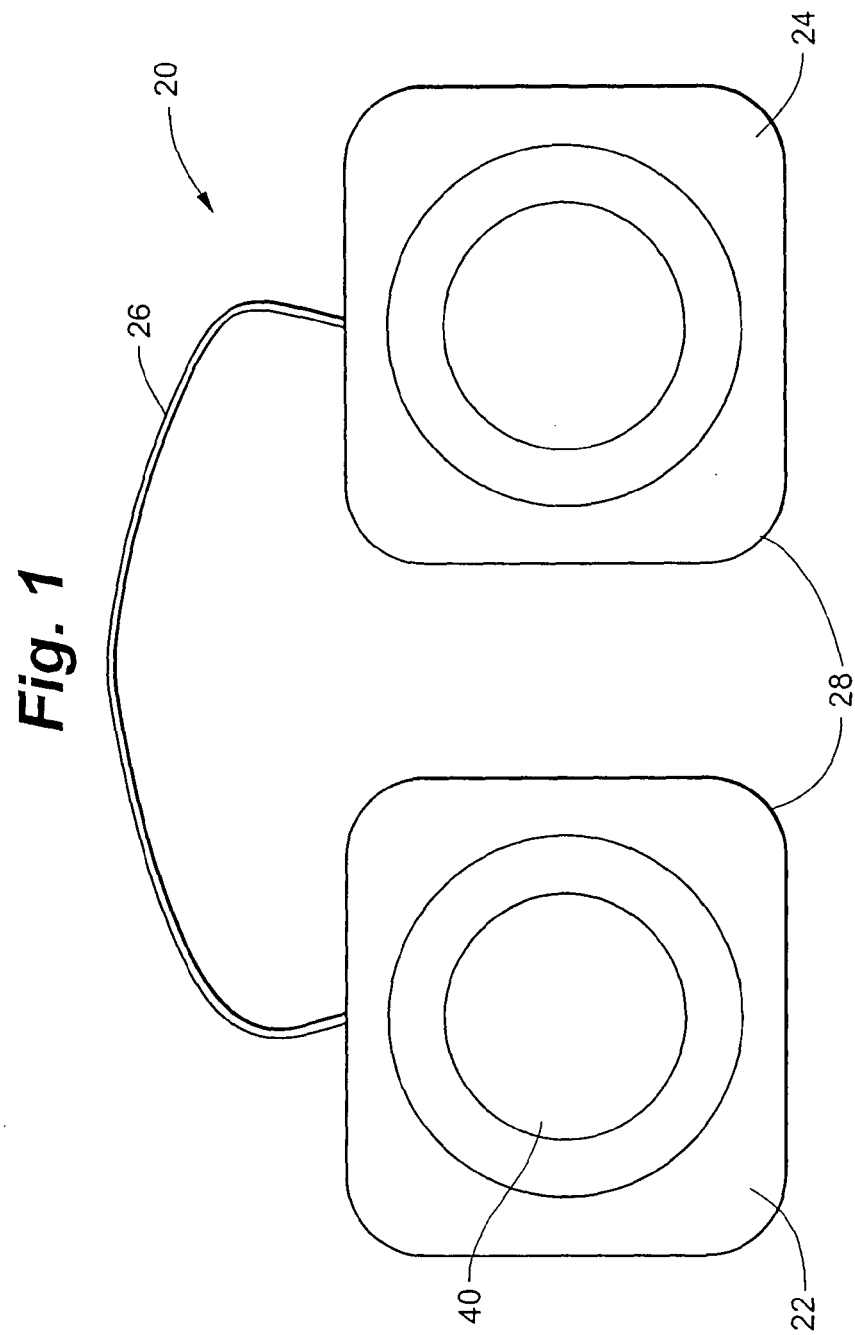

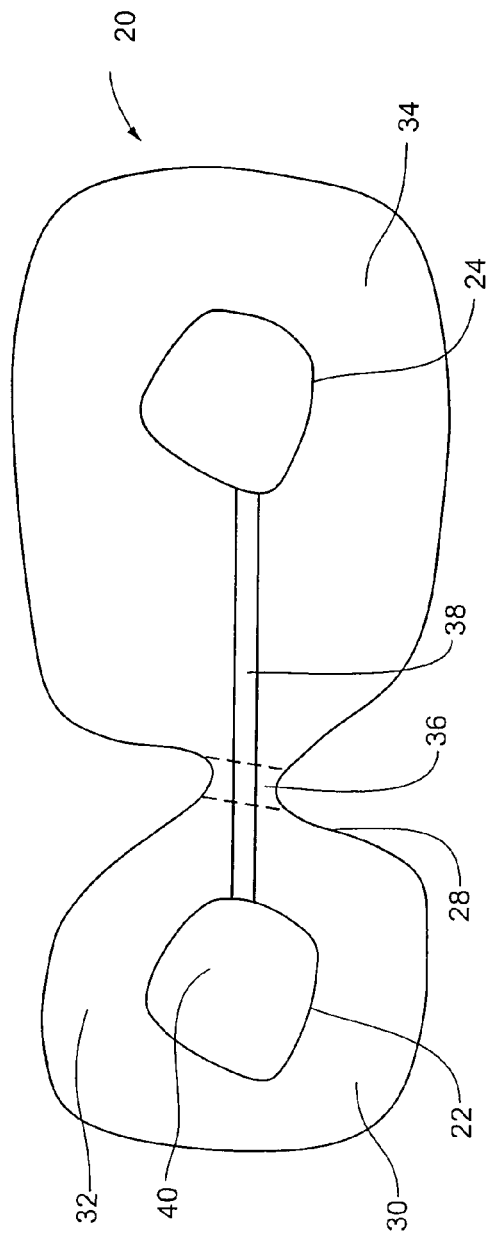
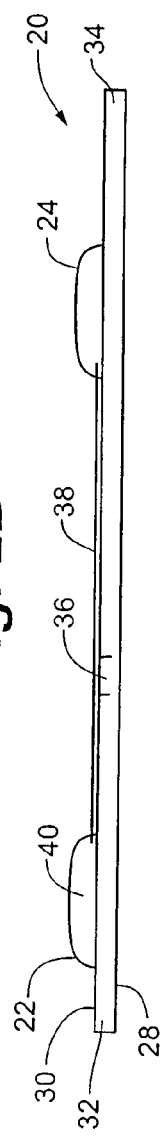

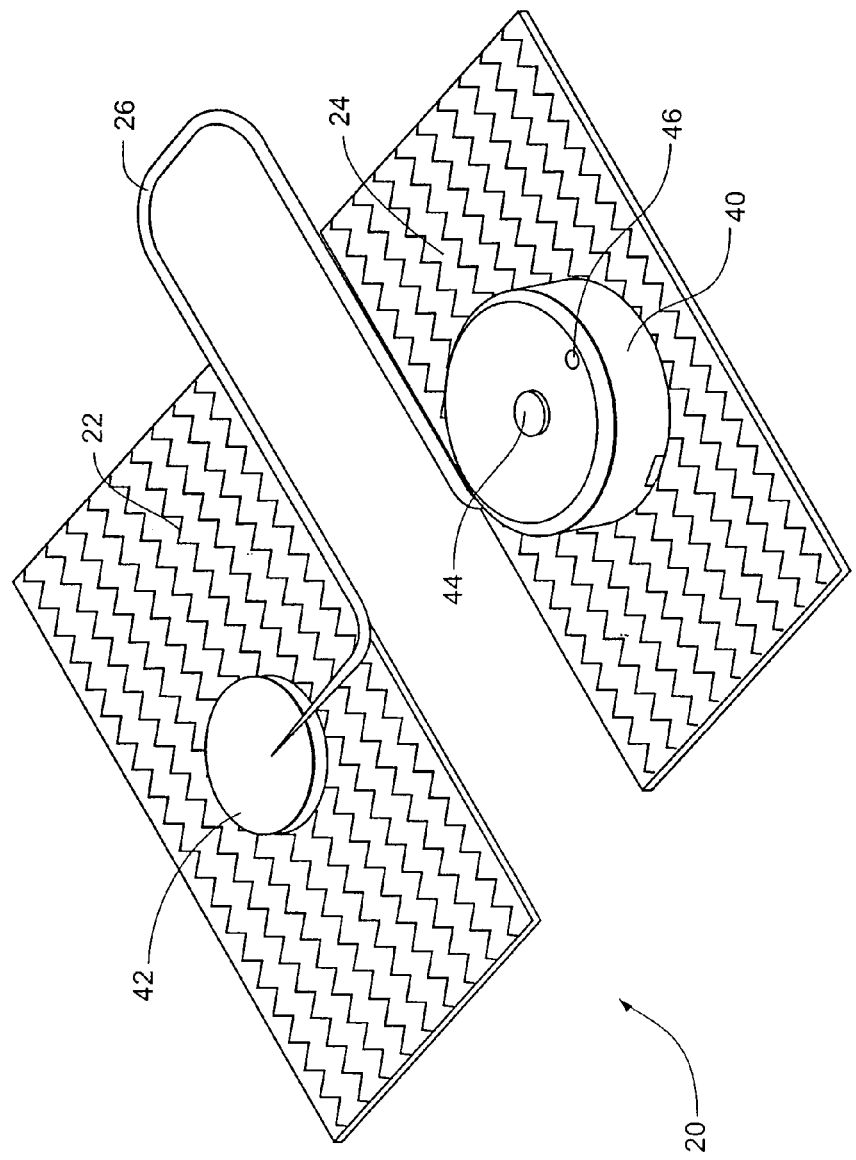

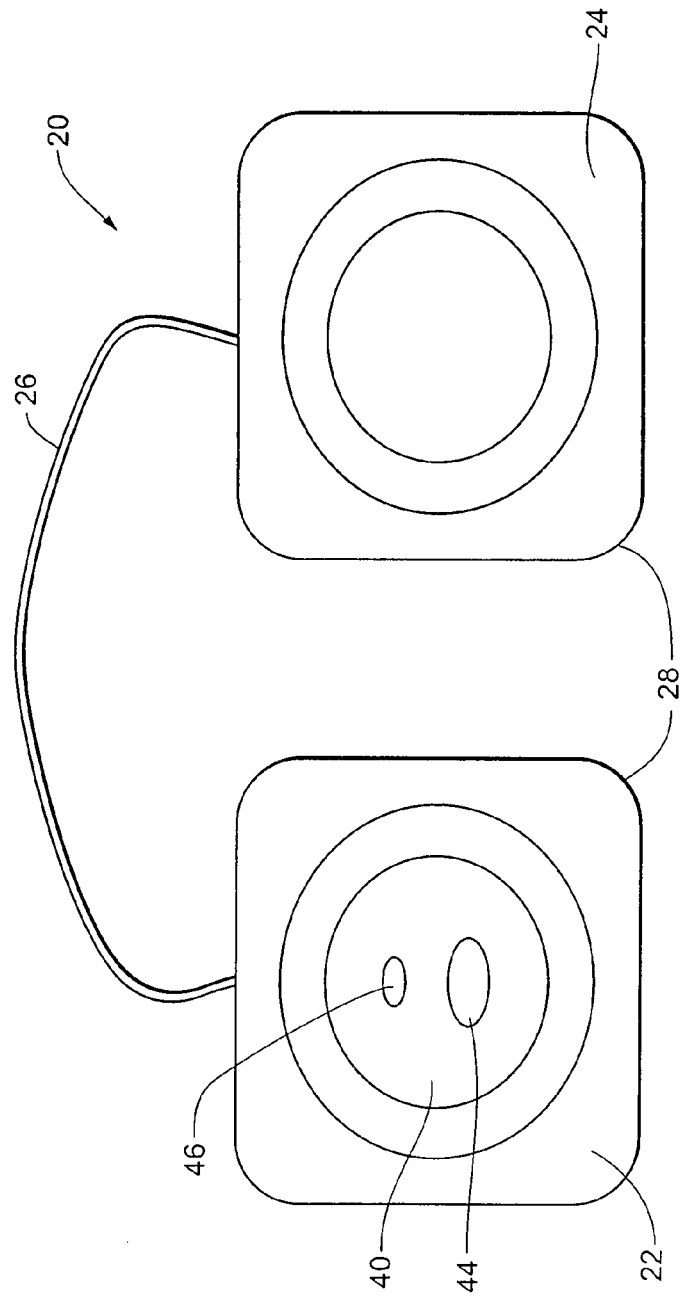

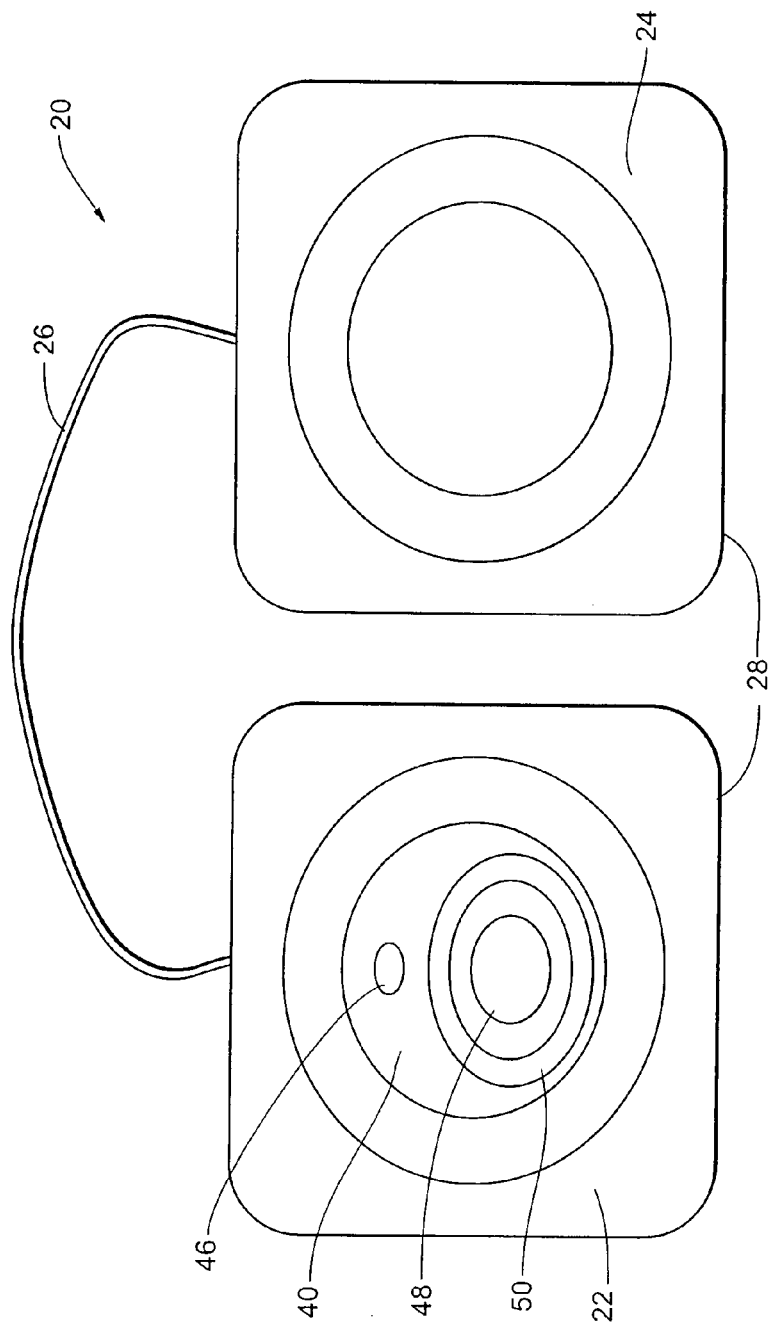

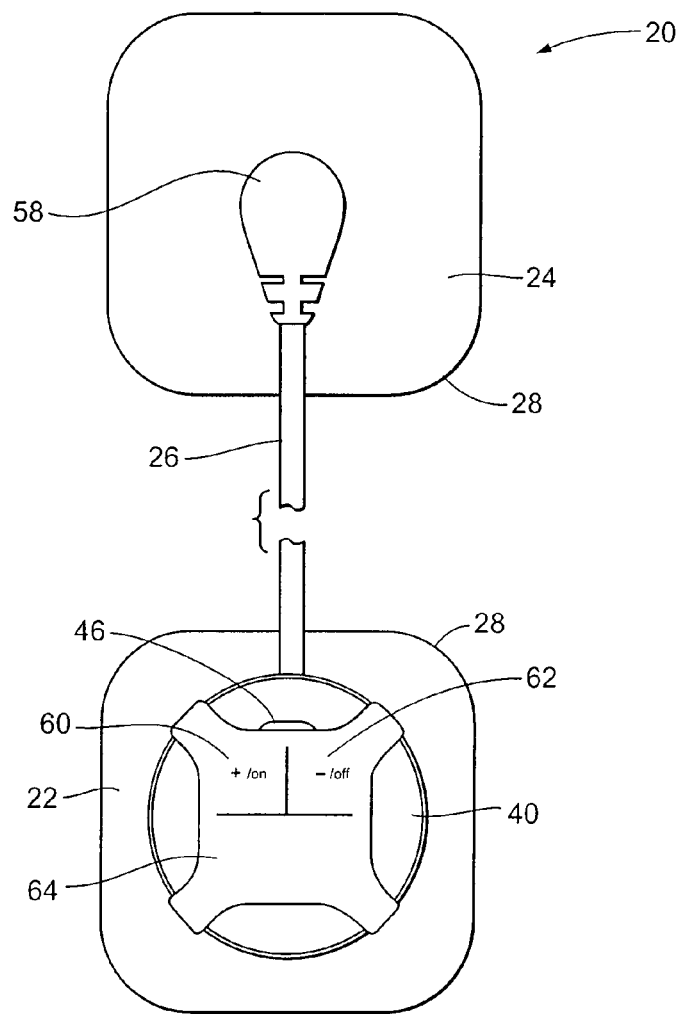

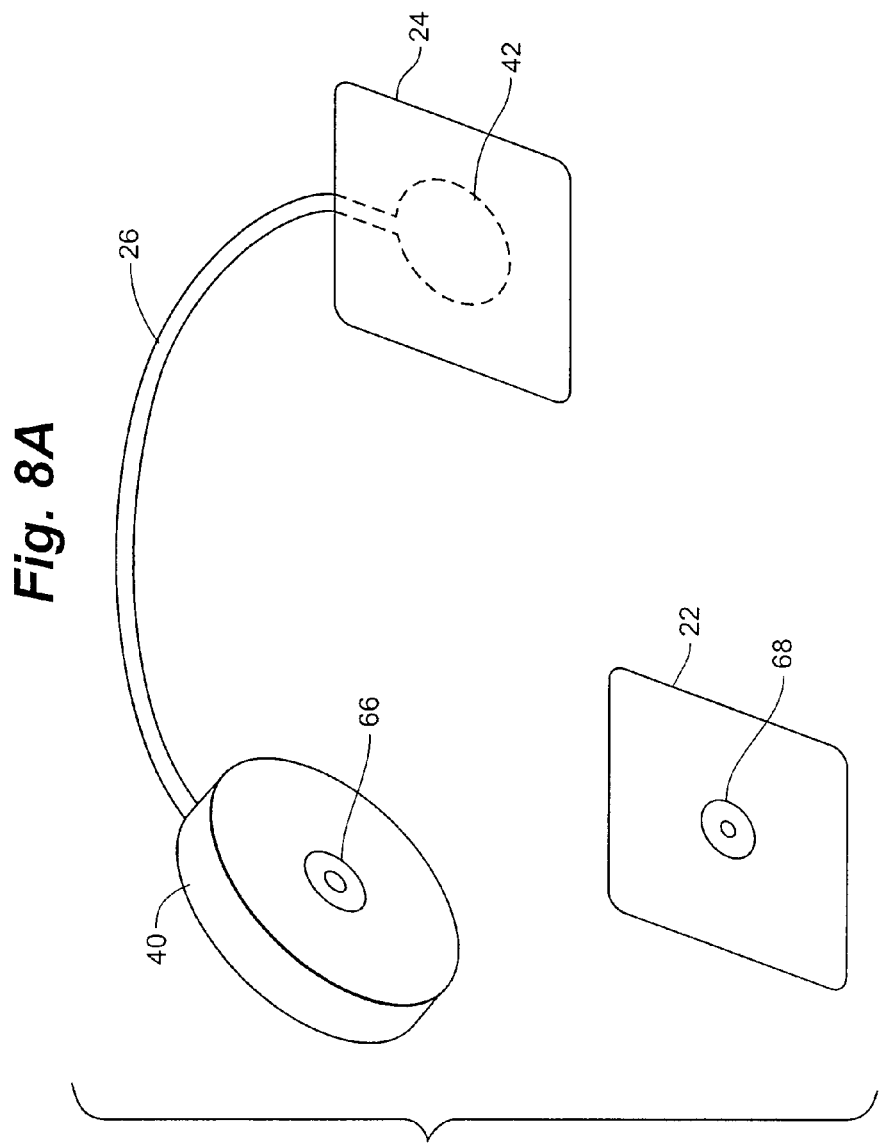

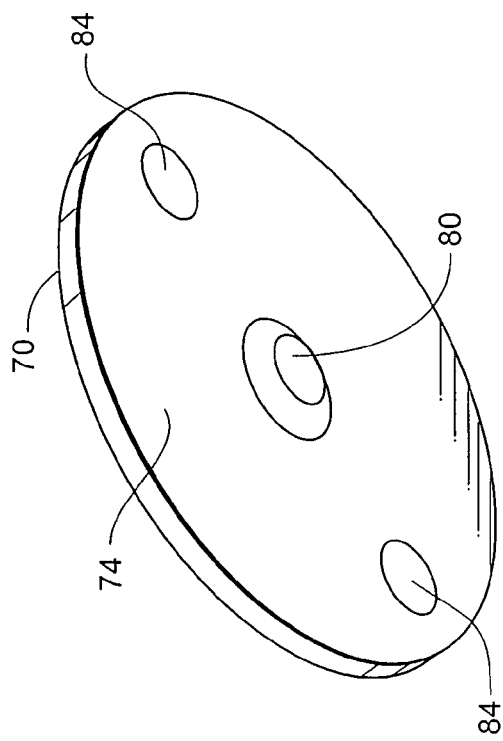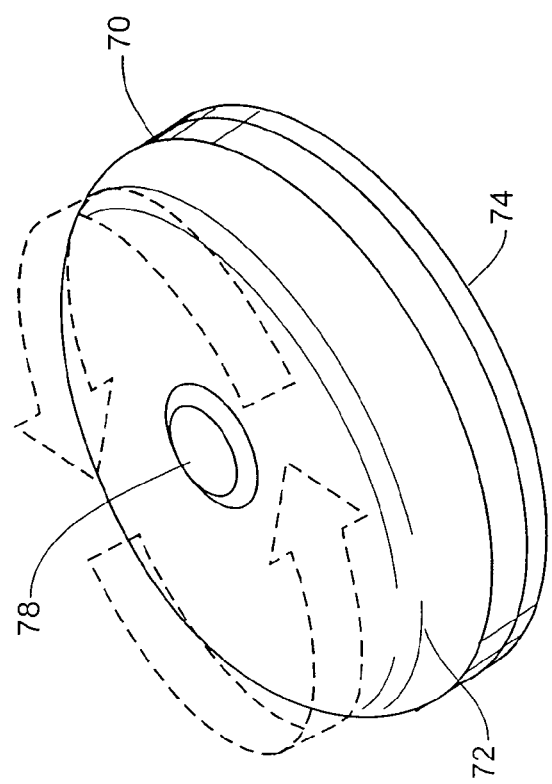

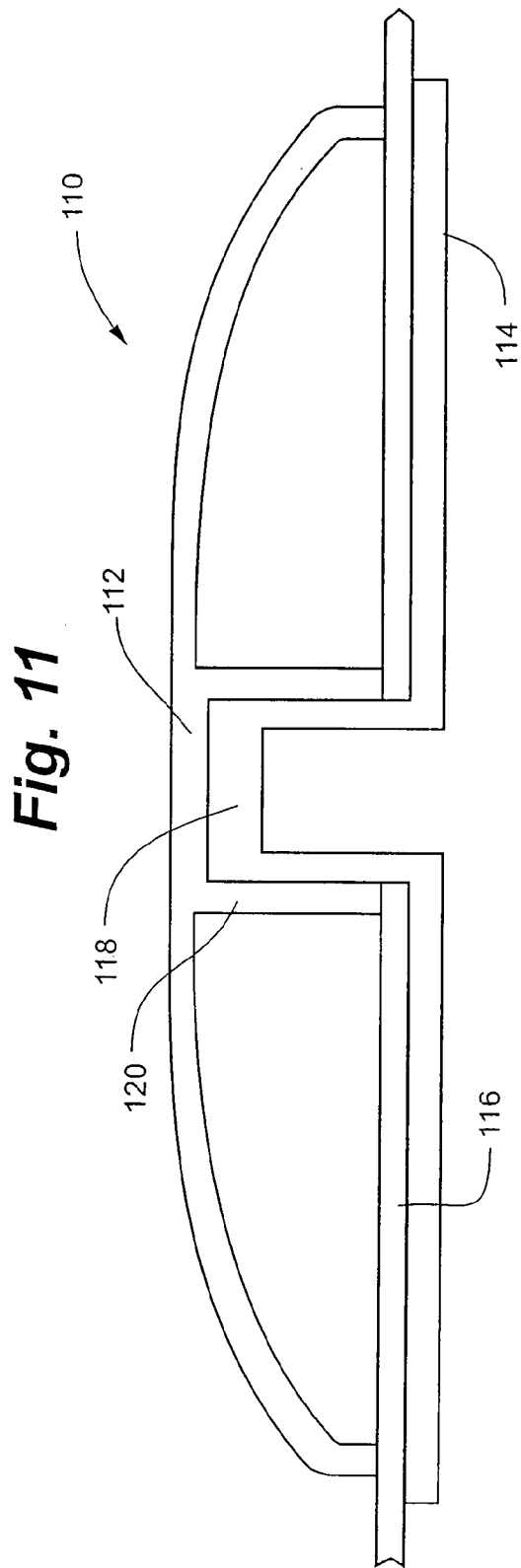

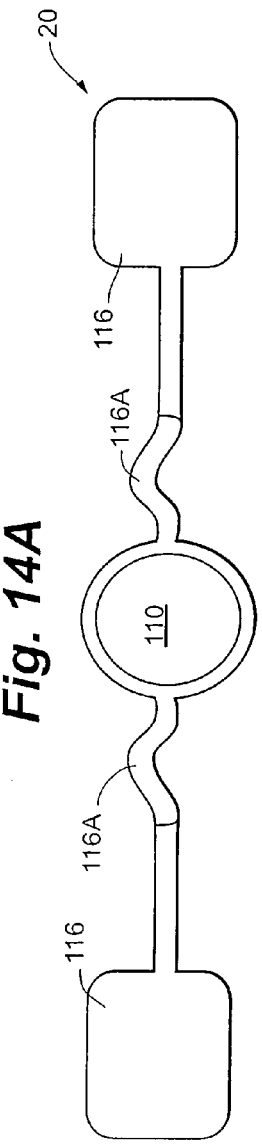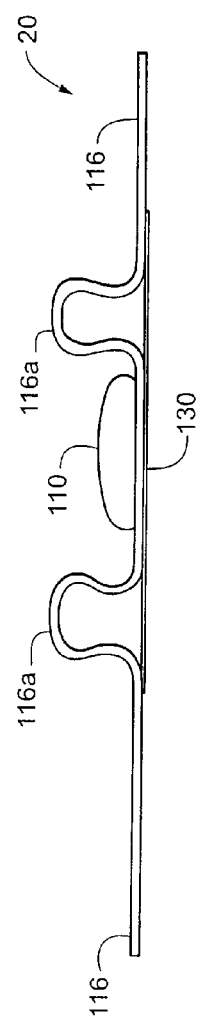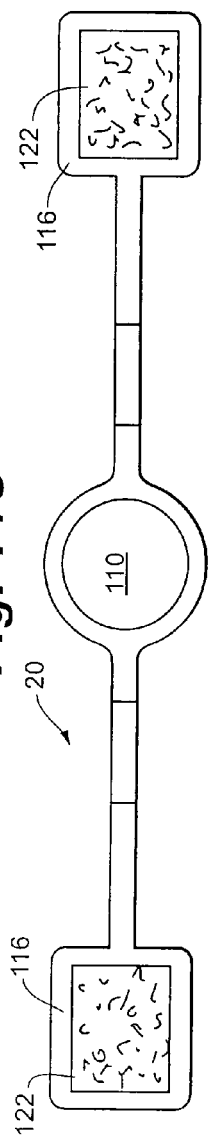

ELECTRICAL STIMULATION DEVICE AND METHOD FOR THERAPEUTIC TREATMENT AND PAIN MANAGEMENT

RELATED APPLICATION

This application claims priority to PCT Application No. PCT/US2006/014734 filed Apr. 19, 2006, and U.S. Provisional Application Serial No. 60/672,937, filed Apr. 19, 2005," the disclosures of which are hereby incorporated by reference in their entireties.

FIELD OF THE INVENTION

The invention relates generally to electrical stimulation for medical purposes. More particularly, the invention is directed to a compact electrical stimulation device and method for controlling and blocking everyday pain.

BACKGROUND OF THE INVENTION

It is common practice for therapists, physicians, athletes, and other individuals to utilize various electrical stimulation treatment and therapy devices to promote muscle training, conditioning, and growth. In addition, devices often referred to as transcutaneous electrical nerve stimulation ("TENS") and microcurrent therapy units are employed to alleviate or eliminate pain and discomfort by blocking nerve signals from an affected area to the brain.

In pain management applications, electrical stimulation devices are used primarily to alleviate pain and discomfort, including chronic intractable pain, post-surgical pain, and post traumatic pain, and to increase blood flow. Increasing blood flow, for example, fosters healing. TENS, microcurrent, and other electrotherapy stimulation techniques have been used successfully for the symptomatic relief and management of chronic intractable pain for many years. In general, TENS or microcurrent electrical nerve stimulation controls pain of peripheral origin by providing a counter stimulation that interferes with the painful sensations.

For example, in one application of electrical stimulation according to gate control theory, small electrical impulses are sent through the skin into a painful area. These electrical impulses are harmless but reach the nerves and cause a mild tingling sensation. Gate control theory provides that as pain impulses travel through a nerve to the spinal cord and brain, the pain impulses can be altered or modified at certain points along the route. Pain signals are carried to the brain via small diameter, slow conducting nerve fibers. This transmission can be blocked by stimulating larger diameter, fast conducting nerve fibers. The signals traveling along the fast conducting nerve fibers normally reach the brain before those traveling along the slow conducting nerve fibers. If the larger fibers are stimulated without much activity of the smaller pain fibers, the "gate" is closed and pain is lessened and/or blocked.

Existing electrical stimulation devices used primarily to alleviate muscle pain or other discomfort, or to otherwise provide therapeutic treatment, typically comprise a stimulation unit coupled to an electrode or set of electrodes adapted to deliver stimulation treatment to the tissue of a user. Stimulation units can be large, table-top or freestanding devices, or relatively small, handheld or belt-mounted devices that are more easily portable. In either case, the units are generally used for some period of time, perhaps several minutes to about an hour, and then stored away when not in use. Many also require supervised use and treatment by a medical professional.

U.S. Pat. Nos. 6,002,965 and 6,282,448 disclose self applied devices and methods for prevention of deep vein thrombosis. The devices comprise an elongated rectangular cuff having fasteners and electrodes with an attached control unit for providing a predetermined electrical signal to the electrodes. The electrodes can also be combined with a motion detector for detecting muscle contraction.

Microcurrent and other therapeutic devices used for pain management are known in patch or bandage form, which are typically less obtrusive and expensive than the aforementioned stimulation units. These devices can easily be worn under clothing or otherwise applied to a user's tissue and left on for longer periods of time, from an hour to two or more days. The period of time for which such a microcurrent device can be left is typically dictated by the power source included with the device. While some microcurrent devices can receive power from independent and external sources, other microcurrent devices include an on-board power source, such as a coin-type battery.

For example, U.S. Pat. Nos. 6,408,211 and 6,606,519 teach microcurrent therapy devices for use in applying a DC current of less than one milliampere between two conductive pads through the tissue of a therapy recipient. The device can include an indicator such as an LED to provide an indication of imperceptible current flow, as taught by U.S. Pat. No. 6,408,211. Other microcurrent therapy devices and/or patch or bandage-type devices are disclosed in U.S. Pat. Nos. 3,472,233; 4,398,545; 4,982,742; 5,423,874; 5,578,065; 6,285,899; and 6,631,294.

Existing electrical stimulation devices, in particular those for pain management and control, suffer from several drawbacks. Microcurrent devices, while typically unobtrusive and convenient to use, generally do not excite nerves or stimulate muscles and therefore cannot provide the sensation and healing of TENS or other stimulation devices. Large and handheld devices, however, are cumbersome and do not provide extended treatment times in an unobtrusive and inexpensive manner. These devices also typically require a prescription or monitored use by a physician or other medical professional. Patch and bandage-type devices can offer more convenience, although the increased convenience typically comes at a higher cost. Further, patch and bandage-type devices do not provide control options; these devices instead deliver one treatment mode and intensity with no customization between on or off, or treatment area-specific modes or varieties.

Accordingly, for these and other reasons, a need exists in the industry for an inexpensive, compact, and controllable electrical stimulation device and method for therapeutic treatment and pain management.

SUMMARY OF THE DISCLOSURE

The present invention solves many of the above described deficiencies and drawbacks inherent with conventional TENS and microcurrent therapy devices and treatments. In particular, various embodiments of the invention are directed to a compact electrical stimulation device and a method of providing electrical stimulation. In one embodiment, the electrical stimulation device comprises a TENS-based stimulator having first and second electrodes, first and second electrode zones, or first and second conductive flexible circuit boards for therapeutic treatment and blocking of pain associated with everyday tasks. In another embodiment, the electrical stimulation device can be used as a massage device or muscle stimulator for goals other than pain management, in combination with or without TENS-based stimulation.

According to one aspect of the invention, the electrical stimulation device is compact, with the control circuitry and power source contained within the electrode(s). In one embodiment, both the electronic circuitry and the power source are embedded within one electrode. In another embodiment, the circuitry and power source are within separate electrodes. In yet another embodiment, the control circuitry is enclosed within a control module that can be removably coupled to an electrode. In this embodiment, the power source can be located within the control module, embedded in an electrode, or removably coupled to an electrode. The power source is preferably one or more batteries, and both the control circuitry and power source are preferably inaccessible to a user.

According to one embodiment of the invention, the electrical stimulation device comprises a disposable dual electrode configuration. The electrical stimulation device is adapted to be temporarily affixed to the skin of a user proximate a target tissue treatment area and, in one embodiment, automatically commences treatment upon placement. A pre-programmed treatment program according to this embodiment gradually increases stimulation intensity to a predefined fixed maximum level and maintains electrical stimulation therapy until the device is removed from a user's skin or a power source is fully depleted. In one embodiment, the power source comprises at least one non-replaceable battery embedded in one or both of the electrodes and has an expected life in continuous use of several hours, typically about twelve hours with a preset intensity level setting. The power source can also be replaceable or rechargeable. After treatment, the electrical stimulation device is fully or partially disposable. In partially disposable embodiments, the electrodes can be disposed of while at least a portion of the control module is reusable. In a fully disposable embodiment, the entire device is non-reusable following depletion of the power source.

According to another embodiment of the invention, the electrical stimulation device further comprises a control button and a status indicator on at least one electrode. The control button can comprise an ON/OFF button, an ON/ADJUST/OFF button, a toggle button, or a plural button configuration. A plural button configuration enables a user to easily and tactilely differentiate between two or more buttons, such as when the electrical stimulation device is positioned on a user's back or other out-of-sight area. In one embodiment, the control button is recessed to prevent accidental activation of the button and also to prevent any metallic contact when a user depresses the button. When the electrical stimulation device is powered on and an ON/ADJUST/OFF button is held, the stimulation intensity can increase until the button is released, up to a preset maximum. When the electrical stimulation device is powered on and a toggle button is depressed, the stimulation intensity step increases to a preset maximum or step decreases to a preset minimum with each depression. In one embodiment, the electrical stimulation device preferably includes several different intensity settings. In another embodiment, the electrical stimulation device provides a continuous ramping up of intensity to a preset maximum. In yet another embodiment, the electrical stimulation device provides a single intensity. In one embodiment, the status indicator is a light-emitting diode (LED). The indicator is preferably illuminated, steady or blinking, when the device is powered on and power source life exists.

Preferred embodiments of the electrical stimulation device of the invention thereby can provide compact and convenient therapeutic treatment devices. The common structure of communicatively coupled dual electrodes including embedded or enclosed circuitry and a power source accommodates a range of different sizes, configurations, stimulation treatment intensities, and other physical and electrical characteristics that can be pre-customized and packaged for specific use.

The device can therefore be used in methods of providing therapy, managing pain, and achieving other treatment goals by electrical stimulation. In particular, one method of providing electrical stimulation therapy thereby can comprise offering a range of various electrical stimulation devices, each customized for a desired therapeutic treatment and/or region of the body, that are inexpensive, unobtrusive, easy to use, and partially or completely disposable. Each device of the range can be packaged for easy identification and selection by a user according to a particular need.

The above summary of the invention is not intended to describe each illustrated embodiment or every implementation of the present invention. The figures and the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 1 is a top view of an electrical stimulation device according to one embodiment of the invention.

FIG. 2A is a top view of an electrical stimulation device according to one embodiment of the invention.

FIG. 2B is a side view of the electrical stimulation device of FIG. 2A.

FIG. 3 is a top perspective view of an electrical stimulation device according to one embodiment of the invention.

FIG. 4 is a top view of an electrical stimulation device according to one embodiment of the invention.

FIG. 5 is a top view of an electrical stimulation device according to one embodiment of the invention.

FIG. 7A is a top view of an electrical stimulation device according to one embodiment of the invention.

FIG. 8A is a perspective view of an electrical stimulation device according to one embodiment of the invention, depicting a snap attachment feature.

FIG. 10A is a top perspective view of the control module of FIG. 9A.

FIG. 10B is a bottom perspective view of the control module of FIGS. 9 and 10A.

FIG. 11 is a side cross-sectional view of a control module housing according to one embodiment of the invention.

FIG. 14A is a top view of the electrical stimulation device of FIG. 13.

FIG. 14B is another side view of the electrical stimulation device of FIGS. 13 and 14A.

FIG. 14C is a bottom view of the electrical stimulation device of FIGS. 13, 14A, and 14B.

Figure 6:
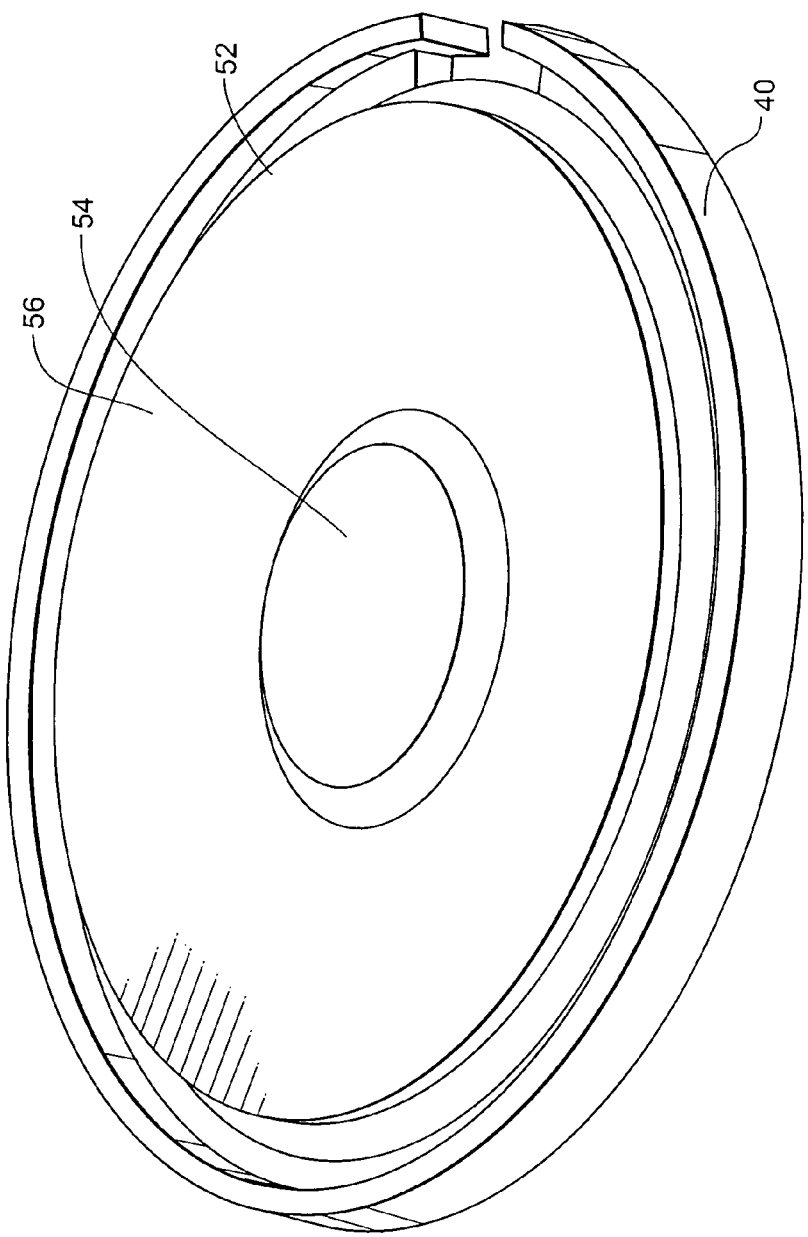
FIG. 6 is an enlarged top perspective view of a keypad according to one embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE INVENTION

The electrical stimulation device and method according to the invention provide inexpensive and convenient therapeutic treatment and pain management. The invention can be more readily understood by reference to FIGS. 1-14C and the following description. While the invention is not necessarily limited to such an application, the invention will be better appreciated using a discussion of exemplary embodiments in specific contexts.

Referring to FIG. 1, an electrical stimulation device 20 comprises an automatic and, in one embodiment, disposable dual electrode configuration. A first electrode 22 and a second electrode 24 are physically and electrically coupled by a flexible cable or lead wire 26. This dual electrode configuration enables placement of device 10 on many different parts of the body to provide electrical stimulation for therapeutic treatment and pain management. To this end, the size and shape of electrodes 22 and 24, and the length of lead wire 26, can vary to more easily conform to a particular area of the body. For example, while substantially square or rectangular electrodes may be suited to the abdomen and back, round, oblong, or substantially I-shaped electrodes may better conform to the shoulders, arms, legs, and other areas of the body. In one example embodiment, electrodes 22 and 24 are approximately two inches, or about five centimeters, square, and lead wire 26 is about six inches, or about fifteen centimeters, long. In another embodiment, electrodes 22 and 24 are each about two (inches) wide and about four inches long, or about five centimeters by about ten centimeters. Electrodes 22 and 24 preferably have a low profile, i.e., are as thin as possible, to remain unobtrusive and invisible when worn, for example, under clothing.

A first surface of each first electrode 22 and second electrode 24 preferably includes an adhesive layer 28 adapted to temporarily affix each electrode 22 and 24 to a user's skin for treatment. In one preferred embodiment, adhesive layer 28 comprises a material that can maintain adherence to a user's skin for a treatment session of a few minutes to several hours or more, withstand movement by the user during the treatment session, and is substantially waterproof yet easily and painlessly removable by a user after treatment. In another preferred embodiment, adhesive layer 28 further comprises a reusable adhesive material such that a user can apply electrodes 22 and 24 for a first treatment session, selectively remove electrodes 22 and 14, and later reapply electrodes 22 and 24 for a second treatment session. Adhesive layer 28 may also include a topical agent, for example menthol or capsaicin, that provides an initial, non-iontophoretic warming or cooling sensation to a user's skin upon application and contact to further alleviate pain.

In another embodiment of device 20 depicted in FIG. 2, electrodes 22 and 24 and lead wire 26 are incorporated into a single structure 30. In this embodiment, structure 30 comprises two distinct active electrode areas or zones 32 and 34 that are isolated from each other by an electrical isolation zone 36. Electrodes 22 and 24, and zones 32 and 34, are electrically coupled, such as by an embedded lead wire 38, or by a flexible circuit board, electrical substrate, or other similar structure. The size, shape, and configuration of structure 30; zones 32, 34, and 36; and lead wire 38 can vary from the embodiment depicted in FIG. 2. For example, structure 30 and the relative placement of zones 32 and 34, and accordingly zone 36 and lead wire 38, can be customized for a particular treatment area of the body, offered in a range of sizes, and the like. Device 20 also includes a control module 40 comprising internal control circuitry, which will be described in more detail below with reference to other figures and embodiments of the invention that include similar features.

Referring again to FIG. 1 in addition to FIG. 2, device 20 is a TENS-based stimulator in one embodiment and comprises stimulation control circuitry internal to a control module 40. In the embodiments of FIGS. 1 and 2, control module 40 is embedded in first electrode 22 and zone 32. It will be appreciated by those skilled in the art that control module 40 can be embedded in or coupled to either or both electrodes 22 and 24 or zones 32 and 34. In other preferred embodiments of the invention, device 20 delivers electrical stimulation modalities other than TENS, for example massage, muscle stimulation, cartilage growth stimulation, bone growth stimulation, and other therapeutic treatments. Embodiments of device 20 can also be used in the aid and treatment of chronic conditions, such as arthritis. Device 20 can also help stimulate blood flow and therefore can be an aid in reduced mobility environments, such as long plane trips, or in recovery from surgery or injury. Control module 40 includes an electrical stimulation signal generator and associated circuitry (internal as viewed in FIGS. 1 and 2) to generate, control, monitor, and deliver electrical stimulation treatment to a user. Embedding control module 40 into one of electrodes 22 and 24 or zones 32 and 34 provides a small, compact electrical stimulation device 20 that is more convenient and less obtrusive than other electrical stimulators.

In another embodiment, a portion of control module 40 is embedded in or coupled to one or both of electrodes 22 and 24, while another portion is removed from electrodes 22 and 24 to operate as a wireless remote control. Such a configuration can be especially convenient when device 20 is to be positioned in an awkward or hard-to-reach part of the body. Control module 40 can also be adapted or customized for particular applications. For example, in one embodiment control module 40 further comprises a heart rate monitor or other body feedback indicator.

Device 20 further comprises a power source (internal), for example one or more coin-type batteries. The power source(s) can be included within control module 40, or remote from control module 40 and housed internal to second electrode 24 or zone 34, or first electrode 22 or zone 32 in another embodiment. For example, as depicted in FIG. 3, a power source 42 is embedded within a first electrode 22, and control module 40 is coupled to a second electrode 24, connected by lead wire 26. The exterior coupling of control module 40 to electrode 24, rather than embedding, is described in more detail below. Power source 42 can be single use and non-replaceable, with device 20 fully disposable upon depletion of power source 42, although in other embodiments device 20 is limited use, capable of being reapplied for subsequent use(s) until limited-capacity power source 42 is fully depleted. In other embodiments, power source 42 is rechargeable and/or replaceable. Power source 42 can comprise a battery, such as a rigid or supple lithium battery, coin battery, or other cell.

In one preferred embodiment, neither control module 40 nor the power source(s) 42 are user accessible, improving the operational integrity of device 20 and providing an elevated level of safety to a user. Device 20 can further be made tamper-evident, rendering device 20 inoperative if a user attempts to access control circuitry 40 and/or power source 42 or to otherwise alter the general operation or configuration of device 20.

In one embodiment, device 20 is programmed to automatically commence treatment upon affixation to the skin of a user. A preprogrammed treatment program in control module 40 according to this embodiment gradually increases stimulation intensity to a predefined fixed maximum level and maintains electrical stimulation therapy until the device is removed from a user's skin or a power source is fully depleted. In one embodiment, the gradual intensity increase to a maximum intensity takes place over a period of about one to several minutes, more specifically about two minutes. The power source can comprise at least one non-replaceable battery embedded in one or both of the electrodes and has an expected life in continuous use of about twelve hours. Other power sources can be used and selected to maximize a desired treatment that may be customized to deliver a longer, shorter, more intense, or less intense stimulation program. After treatment, the electrical stimulation device is partially or completely disposable. For example, control module 40 may be reusable while electrodes 22 and 24 are single use and disposable.

Referring to FIGS. 3 and 4, device 20 according to another embodiment of the invention comprises a control button 44 and a status indicator 46. Control button 44 and status indicator 46 can also be included on structure 30 (FIG. 2). Control button 44 can comprise an ON/OFF button, an ON/ADJUST/OFF button, a toggle or slide, or some other similar configuration. In one preferred embodiment, control button 44 comprises a single-contact depressible ON/OFF button that operates an embedded contact or switch. In this embodiment, device 20 is powered on by depressing button 44 a first time and instantly powered off by depressing button 44 a second time. In one embodiment, control button 44 is recessed to prevent accidental activation and also to prevent any metallic contact when a user depresses button 44.

In another preferred embodiment, control button 44 comprises a single-contact ON/ADJUST/OFF button. In this embodiment, a first depression of the button powers on device 20, a second maintained depression increases or otherwise adjusts a stimulation intensity delivered by device 20, and a third depression powers off device 20. When device 20 is powered on and ON/ADJUST/OFF button 44 is held, the stimulation intensity increases until button 44 is released, up to a preset maximum.

In yet another preferred embodiment, control button 44 comprises a dual- or multi-contact toggle button. The toggle button can be used to power device 20 on and off and to increase or decrease stimulation intensity. When electrical stimulation device 20 is powered on and toggle button 44 of this embodiment is depressed, the stimulation intensity step increases to a preset maximum or step decreases to a preset minimum with each depression.

Referring to the embodiment of FIG. 5, device 20 comprises a first control button 48 and a second control button 50. First control button 48 is an ON/UP adjustment input and second control button 50 is an OFF/DOWN adjustment input, although the particular functions of each first control button 48 and second control button 50 can be reversed, or another configuration can be programmed and implemented. As depicted, button 48 is similar in configuration to control button 44, while button 50 is a ring-type push-activated structure. This dual-function keypad is helpful when device 20 is placed on areas of the body where line of sight is not available, providing an easy way for a user to tactilely differentiate between buttons 48 and 50 to increase or decrease a stimulation intensity or change an operational state of device 20. In contrast, if a single toggle button is implemented and a user cannot see an orientation of device 20 in order to visually determine which side of the toggle to depress, the user may inadvertently increase the stimulation intensity by depressing the wrong side when instead he or she desired to decrease the intensity.

In another embodiment, the dual-function keypad depicted in FIG. 5 can be integrated into a single piece, flexible button. Referring to FIG. 6, an alternate embodiment of control module 40 incorporates a single, dual-function flexible keypad 52. Dual-function keypad 52 comprises a first inner zone 54 (analogous to button 48 of FIG. 5) and a second outer zone 56 (analogous to button 50 of FIG. 5). Control module 40 comprising dual-function keypad 52 as depicted in FIG. 6 can be substituted for the embodiment of control module 40 depicted in FIG. 3, for example. Zones 54 and 56 can be programmed according to functionality that is the same as or similar to that of buttons 48 and 50 described above with reference to FIG. 5. Flexible keypad 52 makes more convenient the placement and operation of device 20.

FIGS. 7A-7F depict additional alternate embodiments of device 20 and control buttons 34 and 36. As in the embodiment depicted in FIG. 3, device 20 of FIGS. 7A-7F comprises control module 40 coupled to a surface of one of electrodes 22 and 24, rather than being embedded within electrode 22 or 24. In one embodiment, a portion of control module 40 is embedded within electrode 22 or 24, while a remainder of control module 40 is mechanically and electrically coupled to electrode 22 or 24 and the embedded circuitry.

Referring to FIG. 7A, device 20 comprises first and second electrodes 22 and 24, control module 40, and lead wire 26 coupling control module 40 and first electrode 22 to second electrode 24. Power source 42 (not shown) can be included within control module 40, or embedded within one of electrodes 22 or 24 or a connector 58, which mechanically and electrically couples lead wire 26 to electrode 24 and is described in more detail below. As depicted, connector 58 can include strain relief means to make more convenient the positioning of electrode 22 relative to electrode 24. In another embodiment, power source 42 can comprise two or more separate batteries or other power supplies, with individual batteries embedded within one or more of electrodes 22 and 24, control module 40, and connector 58.

Figure 7B:
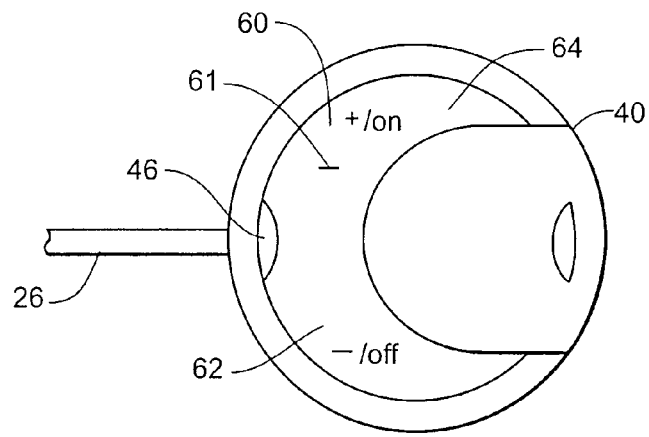
FIG. 7B is a top view of one embodiment of a control module of the electrical stimulation device of FIG. 7A.
Figure 7C:
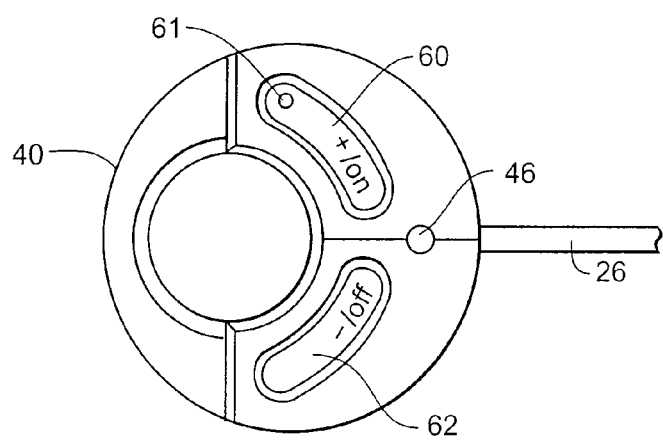
FIG. 7C is a top view of another embodiment of a control module of the electrical stimulation device of FIG. 7A.
Figure 7D:
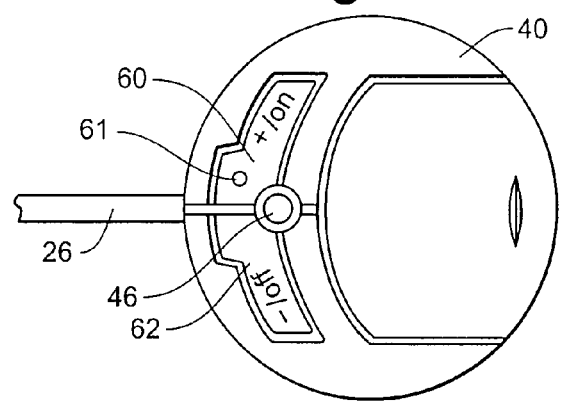
FIG. 7D is a top view of another embodiment of a control module of the electrical stimulation device of FIG. 7A.
Figure 7E:
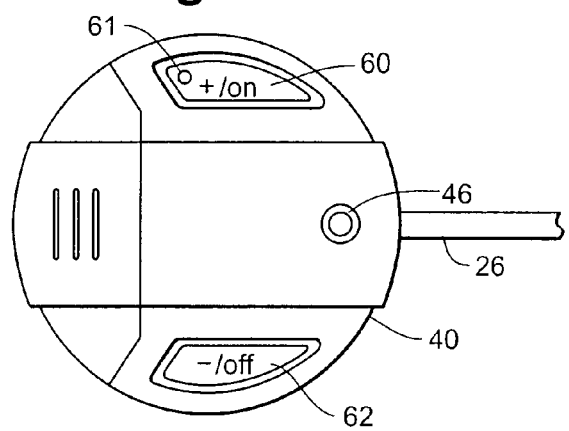
FIG. 7E is a top view of another embodiment of a control module of the electrical stimulation device of FIG. 7A.
Figure 7F:
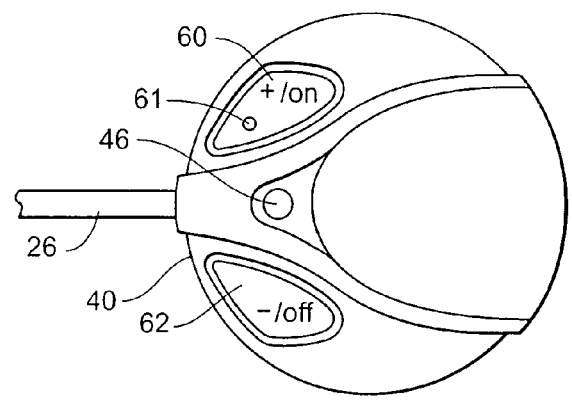
FIG. 7F is a top view of another embodiment of a control module of the electrical stimulation device of FIG. 7A.

Control module 40 as depicted in FIG. 7A comprises a first ON/INCREASE control button 60 and a second OFF/DECREASE control button 62. Buttons 60 and 62 are similar to control buttons 48 and 50 described above. Other button configurations that are tactilely or otherwise differentiated when out of sight can also be used, for example one convex button and one concave button; two other distinctly shaped buttons, such as one round button and one square; one or both buttons having textured or raised surfaces; two distinct materials, such as one plastic-like button and one rubber-like button; and the like. The contact areas of each of buttons 44, 48, 50, 54, 56, 60 and 62, regardless of configuration, are preferably recessed or raised with respect to an outer housing or rim of control module 40 and/or another button for differentiation and to prevent accidental activation, although certain button features may be raised for easier identification. For example, referring to FIG. 7A, button 50 is raised with respect to a housing 64 of control module 40, which button 62 is recessed. In FIGS. 7B-F, button 60 comprises a raised portion 61 to aid in button identification and differentiation.

In one embodiment, control module 40 further comprises status indicator 46. Status indicator 46 preferably provides a visual indication of a power-on state of device 20. In one embodiment, status indicator 46 is a light-emitting diode (LED). Indicator 46 is preferably illuminated, steady or blinking, when the device is powered on and power source 42 life exists. Status indicator 46 can be programmed to provide additional information in other embodiments. For example, in embodiments in which an increased or maximum intensity is blocked by device 20 for an initial warm-up period, indicator 32 can flash during the warm-up period and then be illuminated in a steady state to communicate to a user that the intensity may now be selectively increased. In another embodiment, indicator 32 can flash faster or slower according to a stimulation frequency. In yet another embodiment, control module 40 comprises an audible status indicator instead of or in addition to status indicator 46. Long, short, or steady tones can be used in this embodiment to differentiate various operating states and conditions.

In alternate embodiments, control module 40 comprises one or more embedded status indicators instead of or in addition to external status indicator 46. In these alternate embodiment, all or part of housing 64 of control module 40 is transparent or semi-transparent to permit viewing of the embedded status indicator(s). For example, a first status indicator can be embedded near first control button 60, and a second status indicator can be embedded below second control button 62. The first and second embedded status indicators can then light as either first control button 60 and second control button 62 are activated. The embedded status indicators can comprise LEDs in the same or different colors to differentiate various operating states or functions of device 20. One or more additional embedded status indicators could be positioned within control module 40 below housing 64 to indicate a low battery status, an on or off status, a stimulation frequency or intensity, or some other status, operation, or function. In another embodiment, only a single status indicator is embedded within control module 40 to indicate an on or off state of device 20, as described above with reference to external indicator 46. Whether embedded or external, the single status indicator can also be programmed to flash or change display intensity according to a stimulation treatment being delivered or to otherwise change state according to an operating characteristic of device 20. FIGS. 7B-7F depict alternate embodiments and configurations of control module 40, control buttons 60 and 62, and status indicator 46.

In the embodiments of FIGS. 7A-7F, one or both of electrodes 22 and 24 can be removably or permanently coupled to one or both of control module 40 and connector 58. Removable couplings enable quick and convenient replacement of electrodes 22 and 24, while permanent couplings can improve tamper resistance and security. In one embodiment, a removable coupling is accomplished by a snap connector. As depicted in FIG. 8A, control module 40 comprises a female snap 66 and electrode 22 comprises a male snap 68. Snaps 66 and 68 are adapted to be securely yet removably coupled to each other, providing both mechanical and electrical couplings between control module 40 and electrode 22.

Figure 8B:
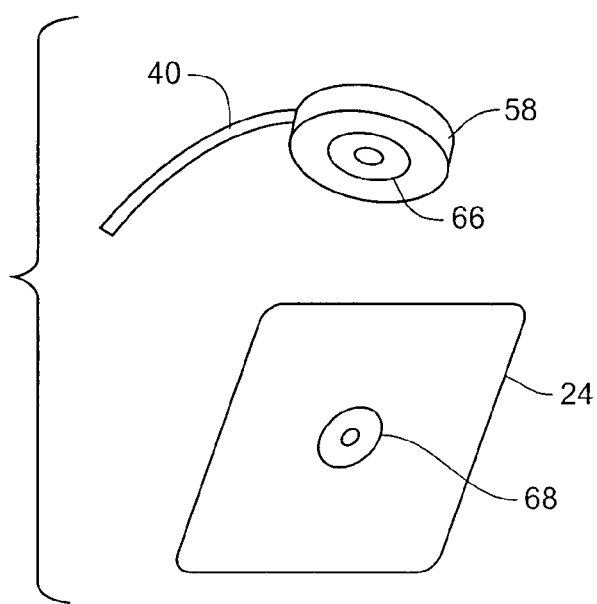
FIG. 8B is a perspective view of another embodiment of the electrical stimulation device of FIG. 8A, depicting another snap attachment feature.

As depicted in FIG. 8A, electrode 24 comprises embedded power source 42. Alternatively, electrode 24 can comprise a male snap 68 adapted to be securely yet removably mechanically and electrically coupled with a female snap 66 on housing 58 (refer also to FIGS. 7A-7F), as depicted in FIG. 8B. In this embodiment, connector 58 can optionally house power source 42 or other circuitry or can comprise a simple mechanical and electrical coupler. Female snap 66 and male snap 68 can also be reversed between control module 40 and electrode 22, and between connector 58 and electrode 24. In one embodiment, snaps 66 and 68 can provide rotation with respect to one another, eliminating the rigid placement structure of electrodes 22 and 24, control module 40 and lead wire 26 and making the positioning of each electrode 22 and 24 on a user's body more convenient.

Figure 9:
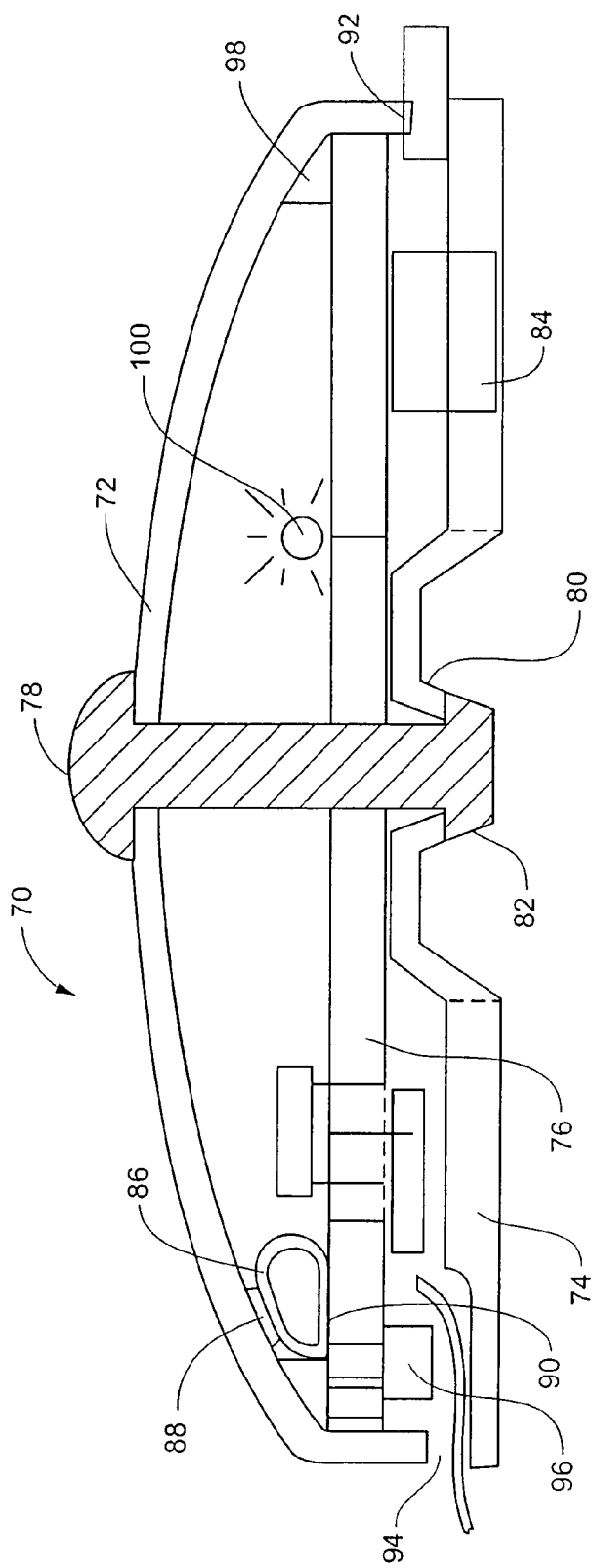
FIG. 9 is a side cross-sectional view of a control module according to one embodiment of the invention.

FIGS. 9-10B depict another preferred embodiment of the electrical stimulation device of the present invention. FIG. 9 is a cross-sectional view of a rotating control module 70, similar to control module 40 above. FIGS. 10A and 10B are top and bottom views, respectively, of control module 70. Control module 70 comprises an upper housing 72 and a lower cover 74 substantially enclosing and protecting control circuitry. Both upper housing 72 and lower cover 74 preferably comprise plastic, textured or coated for improved grip and appearance. The control circuitry within control module 70 comprises a printed circuit board 76 on which a microprocessor and various other electrical components are mounted. A barb rivet 78 can be push-locked to secure upper housing 72, printed circuit board 76, and lower cover 74, and in one embodiment is permanent to prevent a user from accessing or tampering with the internal circuitry. Bottom cover 74 comprises a center snap 80 adapted to interconnect with barb rivet 78. Center snap 80 is preferably sectioned or divided about its circumference to provide adequate flex of the snap feature to interlock with a lower barb 82 of barb rivet 78. Barb rivet 78 secures upper housing 72 to each printed circuit board 76 and lower cover 74 such that upper housing 72 can rotate about barb rivet 78 relative to printed circuit board 76 and lower cover 74. Bottom cover 74 further comprises a second snap portion 84 adapted to removably couple printed circuit board 76 to an electrode (not shown) to deliver electrical stimulation signals and permit replacement of new and used electrodes.

Control module 70 further comprises an internal switch 86 coupled to upper housing 72. In one embodiment, internal switch 86 comprises a foam-filled conductive fabric adhesively secured (78) to upper housing 72, although other switch types and configurations, and other securing means 88 can be used in other embodiments. For example, internal switch 86 can be glued to upper housing 72. Internal switch 72 is configured and placed to activate contacts 90 distributed on printed circuit board 76 when upper housing 72 is rotated relative to printed circuit board 76. Each contact 90 can initiate a different action by the internal circuitry, including ON, OFF, INTENSITY ADJUST UP, INTENSITY ADJUST DOWN, and others. Multiple unique actions are thereby made possible through a simple rotating motion.

In one embodiment, upper housing 72 comprises a wire exit aperture 92 to couple the internal circuitry with an electrode (not shown). A wire or cable passing through wire exit aperture 92 can also provide power if a battery or other power source is located external to control module 70, such as embedded in or mounted on another electrode. In another embodiment, bottom cover 74 comprises a wire exit aperture 84 that permits uninterrupted rotational freedom of upper housing 72 relative to bottom cover 74.

Bottom cover 74 also can comprise mounting points 96 for printed circuit board 76 that do not inhibit rotational movement yet secure printed circuit board 76 and create an air gap within control module 70 for component placement. Mounting points 96 can be molded as part of bottom cover 74, or otherwise secured to both bottom cover 74 and printed circuit board 76. To further secure printed circuit board 76, upper cover 72 can comprise one or more stop ribs 98. Stop ribs 98 keep printed circuit board 76 from floating within control module 70 and can also set limits on rotational motion of upper cover 72 by abutting corresponding ribs (not shown) on printed circuit board 76. Stop ribs 98 can also be used to create a ratchet effect, locking or free motion, to control and indicate relative rotational placement in use.

Printed circuit board 76 preferably comprises an indicator 100, such as an LED and similar to indicator 46 described above. In one embodiment, indicator 100 visually distinguishes various operating modes or states by displaying a different color or by blinking. In an embodiment comprising indicator 100, at least a portion of upper housing 72 preferably is transparent or semitransparent to provide control module 70 with a glowing effect or to show a non-steady state of indicator 96.

Figure 12C:
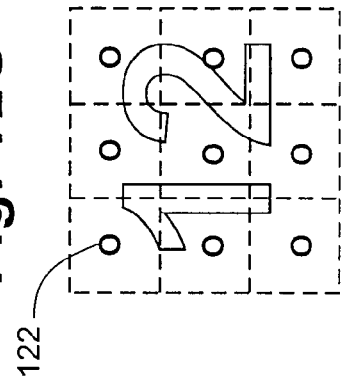
FIG. 12 is a diagram of a plurality of conductive zones according to one embodiment of the invention.
Figure 12B:
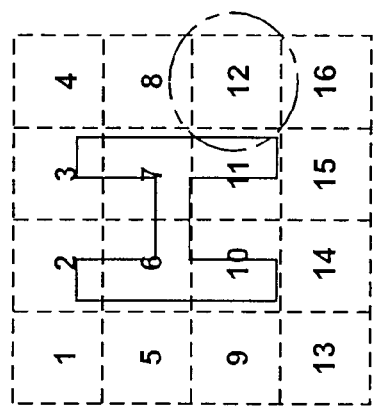
Figure 12A:
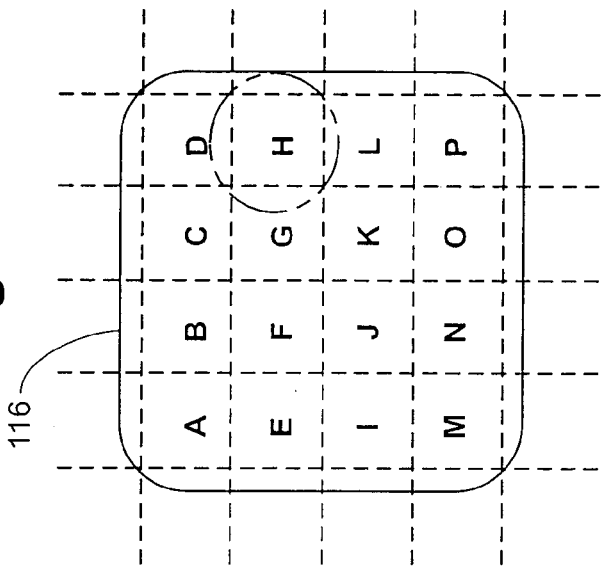
Figure 13:
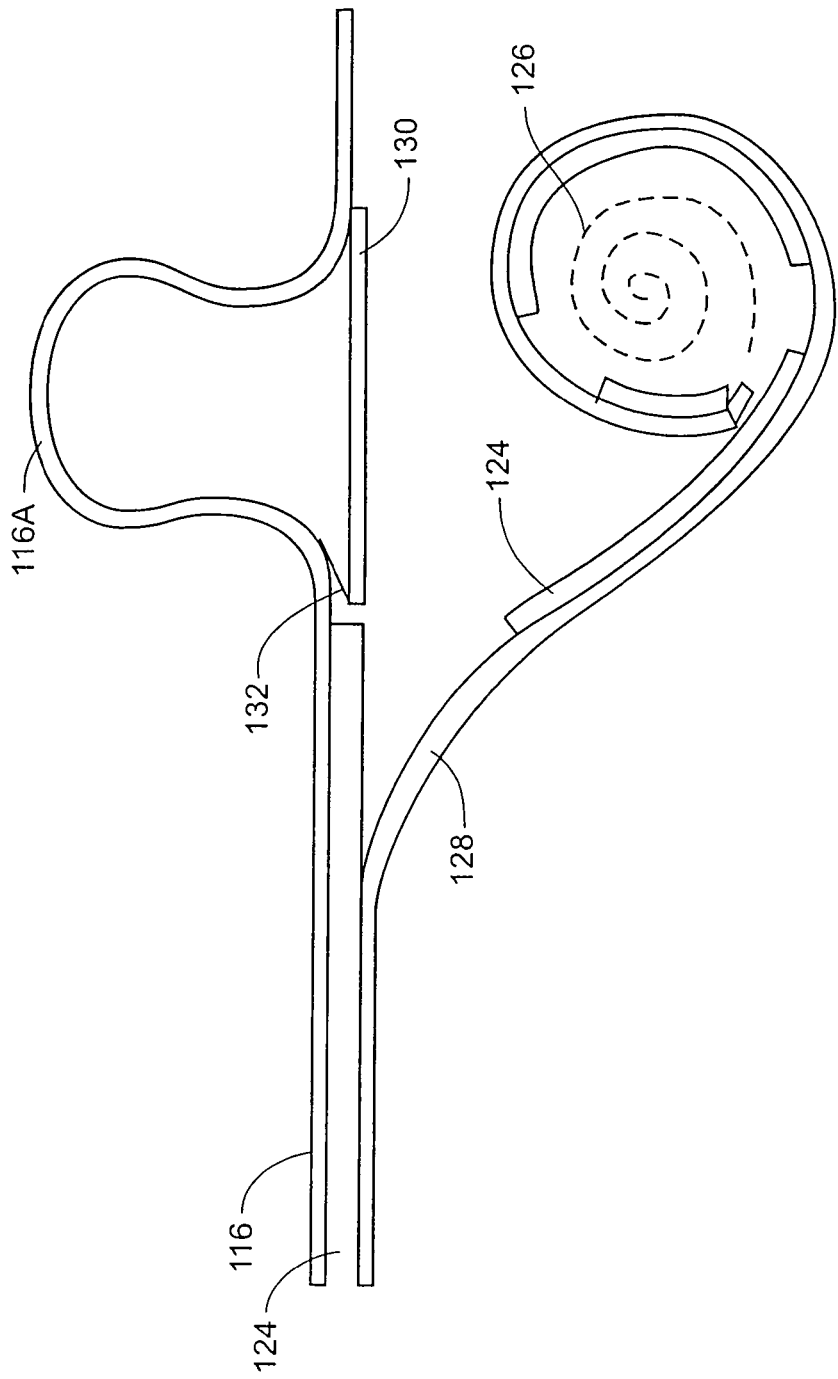
FIG. 13 is a side view of an electrical stimulation device according to one embodiment of the invention.

Yet another embodiment of the electrical stimulation device of the present invention is depicted in FIGS. 11-14C. Device 20 of FIGS. 11-14C comprises a substantially flexible circuit board for even and controlled distribution of electrical stimulation signals. Referring to FIGS. 11-13, a cross-sectional view of a control module 110 similar to control modules 40 and 70 described above is shown. Control module 110 comprises an upper housing 112, a lower cap 114, and a flexible circuit board 116. Upper housing 112 and lower cap 114 substantially enclose circuit board 116, with a male snap portion 118 lower cap 114 secured to a female snap portion 120 of upper housing 112. Snap portions 118 and 120 fit securely yet provide enough clearance for lower cap 114 to freely rotate.

Flexible circuit board 116 comprises a mounting point for the electrical circuitry and components housed in control module 110 and distributes electric current to various conductive zones A-P to simulate an electrode. Each zone A-P is divided into subzones 1-16, and each subzone 1-16 of each zone comprises an array of individual contacts 122. Individual contacts 122 provide a plurality of contact points between device 20 and a user's skin. Advantageously, each contact 122, subzone 1-16, and zone A-P depicted in FIG. 12 can be monitored, controlled, or disabled individually, and a more balanced and efficient distribution of therapeutic current can be provided. Flexible circuit board 116 is therefore an inexpensive alternative to ordinary disposable electrodes.

A conductive electrode adhesive gel 124 can provide adhesion of flexible circuit board 116 to a user's skin and can be easily applied from a roll 126 having a backing 128. Backing 128 can be used to store adhesive gel 124, providing protection from damaging moisture and contamination until use. In one embodiment, conductive adhesive gel 124 can be packaged on backing 128 in precut shapes. After use, adhesive gel 124 can be peeled off of flexible circuit board 116 and discarded and a new layer 114 can be applied.

Referring also to FIGS. 14A-14C, flexible circuit board 116 and control module 110 are mounted to a stretch layer 130. Stretch layer 130 can comprise a fabric or other flexible, elastic material, and flexible circuit board 116 and control module 110 can be secured to layer 130 by an adhesive 132. Stretch layer 130 is designed to provide additional length or to take up any slack in flexible circuit board 116, accommodating various placement distances of the simulated electrode portions of flexible circuit board 116. For example, an extra length 116A of flexible circuit board 116 secured to stretch layer 130 provides easy adjustment of the individual placement and separation distance of two regions of contact zones 122.

Referring now to the various embodiments of FIGS. 1-14C, device 20 preferably includes a plurality of selectable intensity settings when in use, ranging from a preset initial minimum intensity to a preset selectable maximum intensity. In one embodiment, device 20 includes several intensity settings selectable via control button(s) 44, 48/50, 54/56, or 60/62 or via rotatable control module 40. In another embodiment, device 20 provides a continuous ramping up or down of intensity to a preset maximum. The continuous ramping can be automatic, upon initiation of electrical stimulation or after a preprogrammed period of time at a minimum warm-up intensity has passed, or can commence upon user input to control button(s) 44, 48/50, 54/56, or 60/62 or rotatable control module 40, at any time during treatment or after a preprogrammed period of time. The intensity adjustment feature of control button(s) 44, 48/50, 54/56, and 60/62 and rotatable control module 40 may or may not be included in every embodiment of device 20.

In one embodiment, device 20 is adapted to deliver a one-channel, non-compensated but alternated pulse form output across a 500-Ohm load. Various aspects of device 20, both physical and electrical, can be further customized for a particular area of the body or stimulation type. Different varieties of intensity, pulse width, frequency, and other electrical characteristics of the delivered stimulation signals and different electrode shapes and configurations can be provided according to an intended use or application. In any of an automatic, controllable, or other embodiment of electrical stimulation device 20, control modules 40, 70, and 110 can be preprogrammed with one or more of a variety of electrical stimulation treatment programs.

For example, a TENS-based electrical stimulation treatment program can comprise a signal frequency modulated from about sixty-five Hertz (Hz) (130 pulses per second) to about one Hz (two pulses per second) and then back to about 130 Hz with a pulse width of about thirty microseconds in a cycle of about twelve seconds, with a non-linear frequency progression. Device 20 can then be customized to include electrodes 22 and 24, structure 30, or flexible circuit board 116, of various sizes and configurations. In one embodiment, electrodes 22 and 24 are each about four inches long and about two inches wide, or about ten centimeters by about five centimeters, which can be more comfortable for larger muscle areas such as the back and legs. In another embodiment, electrodes 22 and 24 are each about two inches square, or five centimeters by five centimeters, which can be comfortable on other, smaller muscle areas. The overall shape and size of structure 30, one embodiment of which is depicted in FIG. 2, can vary according to almost any configuration. Other sizes and configurations of electrodes 22 and 24 and structure 30 can also be used. The size, shape, and general configuration of flexible circuit board(s) 116 of device 20 can also vary.

In another exemplary embodiment, device 20 provides therapeutic massage by delivering an electrical stimulation treatment program comprising a frequency of about two Hz, four pulses per second, and a pulse width of about 200 microseconds. In this embodiment, device 20 preferably includes the smaller sized electrodes 22 and 24 as described above but can also include the larger or some other electrode size and configuration or structure 30.

In other embodiments, other frequencies, pulse widths, pulse numbers, and other electrical characteristics can be implemented, alone or in combination, to achieve desired therapeutic goals. Other physical characteristics of device 20, such as electrode 22 and 24, structure 30, and flexible circuit board 116 configurations, can also be used. Such characteristics, configurations, and variations of the same can be appreciated by those skilled in the art.

Device 20 can therefore be configured and used for drug- and chemical-free TENS-based pain management applications, or for therapeutic massage, muscle stimulation and contraction, vascular treatment, and other applications. In one embodiment, the length of lead wire 26 or 38, or flexible circuit board 116, can also be customized to make it easier to place device 20 on a particular region of the body. Accordingly, various configurations of device 20 can be offered as a series of customized treatment devices to provide a range of options to users. These devices 20 can be electrically and physically configured for a particular therapeutic treatment and muscle area, then packaged and labeled accordingly for easy identification and selection by a user according to his or her treatment needs. A single device, however, can provide near universal application to all parts of the body in one preferred embodiment.

In use, electrodes 22 and 24, and/or structure 30 and flexible circuit board 116, of device 20 are applied to a user's skin proximate a target tissue treatment area. Device 20 can then be powered on via control button(s) 44, 48/50, 54/56, or 60/62, or rotatable control module 40, to provide electrical stimulation treatment until power source 42 is depleted or device 20 is selectively removed from the user's skin. The power-on and/or operational status of device 20 can be communicated to the user by indicator 46/100. In one preferred embodiment, device 20, in particular control module 40/70/110, includes a load contact detection device, which prevents device 20 from delivering stimulation treatment until device 20 is successfully positioned and applied, i.e., both electrodes 22 and 24, both zones 32 and 34, or both conductive arrays of flexible circuit boards 116, are properly affixed to a user's skin, and which automatically returns a stimulation intensity to zero if one or both of electrodes 22 and 24, zones 32 and 34, or conductive arrays of flexible circuit boards 116, are separated or removed from a user's skin during treatment. In the latter situation, indicator 46/100 will remain on but will change status, for example will change from a steady lighted state to a blinking state, to alert a user. In one preferred embodiment, indicator 40/100 will blink in this state for a limited period of time, such as several seconds to several minutes, more particularly about one minute, before automatically powering off. In another preferred embodiment, device 20 fully and automatically powers off if one or both of electrodes 22 and 24 are removed from a user's skin. Device 20 may then be restarted upon proper reapplication of electrodes 22 and 24. These features thereby improve the safety and power source life of device 20.

In another embodiment as described above, control button(s) 44, 48/50, 54/56, or 60/62 is depressed, or rotatable control module 40 is rotated, to power on device 20 after placement and, if available, to select a desired treatment intensity. As previously described, an upper range or maximum treatment intensity can be blocked for some initial or warm-up period of time, for example about one to several minutes, to allow a user to become acclimated to the electrical stimulation without over-stimulation. Device 20 can then be worn unobtrusively for a desired treatment period, which can be several minutes to several hours or more, while electrical stimulation treatment is continuously provided. In one embodiment, device 20 provides uninterrupted treatment for one day, or about twelve hours. Power-on status and/or power source status can be monitored via indicator 46/100. Treatment can then be selectively stopped by depressing control button(s) 44, 48/50, 54/56, or 60/62 or rotating rotatable control module 40 and, in one embodiment, device 20 can be removed and later reapplied for additional treatment pending power source availability. Treatment may therefore be provided in multiple shorter treatment sessions over a one- or two-day period, according to power source life. Device 20 preferably also includes safety features to prevent electric shock to a user when applying or removing device 20. When a treatment session is complete and/or the power source is depleted, device 20 can be removed and fully or partially disposed. For example, in one embodiment the power source and electrodes are disposable, while control module 40 is at least partially reusable. In other embodiments, device 20 is otherwise partially disposable or is alternately completely disposable.

The electrical stimulation device of the present invention is therefore of benefit in the treatment of nerves, muscles, and other tissues. In various embodiments of the invention, the device delivers TENS and/or other electrical stimulation modalities, for example massage, muscle stimulation, cartilage growth stimulation, bone growth stimulation, and other therapeutic treatments. Embodiments of the device can also be used in the aide and treatment of chronic conditions, such as Arthritis, and to help stimulate blood flow. The device therefore can be an aid in reduced mobility environments, such as long plane trips, or in recovery from surgery or injury.

Although specific embodiments have been illustrated and described herein for purposes of description of an example embodiment, it will be appreciated by those of ordinary skill in the art that a wide variety of alternate and/or equivalent implementations calculated to achieve the same purposes may be substituted for the specific embodiments shown and described without departing from the scope of the present invention. Those skilled in the art will readily appreciate that the invention may be implemented in a very wide variety of embodiments. This application is intended to cover any adaptations or variations of the various embodiments discussed herein, including the disclosure information in the attached appendices. Therefore, it is manifestly intended that this invention be limited only by the claims and the equivalents thereof.

The invention claimed is:

1. A compact electrical stimulation device comprising:
   a first and a second disposable and self-adhesive flexible circuit board comprising an electrode portion and an extra length portion;
   a control module electrically coupled to the electrode portions and comprising: at least one preprogrammed treatment program comprising at least one customizable treatment characteristic;
   a stretch layer, wherein the electrode portions of the flexible circuit boards are mounted to either end of the stretch layer, wherein the control module is mounted on the stretch layer between the electrode portions wherein the stretch layer is configured to provide additional length or to take up any slack in accommodating various placement distances of the electrode portions, and wherein the extra length portions of the circuit boards are not mounted to the stretch layer;
   a status indicator adapted to indicate at least one of a characteristic of the device and a characteristic of the preprogrammed treatment program; and
   a first control input configured to increase a level of the at least one customizable treatment characteristic and a second control input configured to decrease a level of the at least one customizable treatment characteristic, wherein the at least one treatment characteristic is customizable within a predetermined range, the first control input having a first contact area with a first set of tactile features, the second control input having a second contact area with a second set of tactile features, wherein the first set of tactile features comprises a different surface feature than the second set of tactile features, and wherein the first set of tactile features and the second set of tactile features are configured to enable a user to differentiate between the first control input and the second control input when the compact electrical stimulation device is positioned on an out-of-sight area of the user's body such that the user cannot utilize a visually-determined orientation of the compact electrical stimulation device to distinguish the first control input from the second control input;

a power source housed in a structure also having the control module and electrically coupled to the control module to power the electrical stimulation device.

2. The compact electrical stimulation device of claim 1, wherein the power source is replaceable.

3. The compact electrical stimulation device of claim 1, wherein the at least one preprogrammed treatment program is selected from a group consisting of a transcutaneous electrical nerve stimulation (TENS) program, a muscle stimulation program, a massage program, a bone growth stimulation program, and a cartilage growth stimulation program.

4. The compact electrical stimulation device of claim 1, wherein the control module comprises a transparent or semi-transparent housing, and wherein the status indicator is embedded within the control module housing.

5. The compact electrical stimulation device of claim 1, further comprising a strain relief connector proximate the second end, the strain relief connector including a snap connector selectively attachable to a corresponding snap connector of the second electrode portion.

6. The compact electrical stimulation device of claim 1, wherein the control module comprises a snap connector selectively attachable to a corresponding snap connector of the first electrode portion.

7. The compact electrical stimulation device of claim 1, wherein the at least one customizable treatment characteristic comprises a stimulation intensity, and wherein the predetermined range varies from a preset minimum stimulation intensity to a preset maximum stimulation intensity.

8. The compact electrical stimulation device of claim 1, wherein the first control input comprises a depressible outer ring portion of a keypad and the second control input comprises a depressible inner button portion of the keypad.

9. The compact electrical stimulation device of claim 1, wherein one of the first and second sets of tactile features comprises a convex surface, and the other of the first and second sets of tactile features comprises a concave surface.

10. The compact electrical stimulation device of claim 1, wherein the first set of tactile features comprises a different texture than the second set of tactile features.

11. The compact electrical stimulation device of claim 1, wherein the first control input comprises a different material than the second control input.

12. The compact electrical stimulation device of claim 1, wherein one or more of the first and second sets of tactile features is a control button that is recessed or raised with respect to an outer housing or rim of the control module.

13. The compact electrical stimulation device of claim 1, wherein the stretch layer is a fabric.

14. The compact electrical stimulation device of claim 1, wherein the stretch layer is a flexible, elastic material.

15. A compact and disposable electrical stimulation device comprising:
a first and a second disposable and self-adhesive flexible circuit board comprising an electrode portion and an extra length portion;
a control module integrated with the electrode portions and comprising: at least one preprogrammed treatment program comprising at least one customizable treatment characteristic;
a stretch layer, wherein the electrode portions of the flexible circuit boards are mounted to either end of the stretch layer, wherein the control module is mounted on the stretch layer between the electrode portions wherein the stretch layer is configured to provide additional length or to take up any slack in accommodating various placement distances of the electrode portions, and wherein the extra length portions of the circuit boards are not mounted to the stretch layer;
a first control input configured to increase a level of the at least one customizable treatment characteristic and a second control input configured to decrease a level of the at least one customizable treatment characteristic, wherein the at least one treatment characteristic is customizable within a predetermined range, the first control input having a first contact area with a first set of tactile features, the second control input having a second contact area with a second set of tactile features, wherein the first set of tactile features comprises a different surface feature than the second set of tactile features, and wherein the first set of tactile features and the second set of tactile features are configured to enable a user to differentiate between the first control input and the second control input when the compact electrical stimulation device is positioned on an out-of-sight area of the user's body such that the user cannot utilize a visually-determined orientation of the compact electrical stimulation device to distinguish the first control input from the second control input; and
a power source electrically coupled with the control module and integrated with one of the first or second electrode portions.

16. The compact electrical stimulation device of claim 15, wherein the at least one preprogrammed treatment program is selected from a group consisting of a transcutaneous electrical nerve stimulation (TENS) program, a muscle stimulation program, a massage program, a bone growth stimulation program, and a cartilage growth stimulation program.

17. The compact electrical stimulation device of claim 15, wherein the control module further comprises a status indicator adapted to indicate at least one of a characteristic of the device and a characteristic of the preprogrammed treatment program.

18. The compact electrical stimulation device of claim 15, wherein the first and second electrode portions are coupled together by an integral electrical isolation portion.

19. The compact electrical stimulation device of claim 18, wherein the flexible cable is embedded within the first and second electrode portions and the isolation portion.

20. The compact electrical stimulation device of claim 15, wherein the first set of tactile features comprises a different surface feature than the second set of tactile features.

21. A compact electrical stimulation device comprising:
a first and a second disposable and self-adhesive flexible circuit board comprising an electrode portion and an extra length portion;

a control module electrically coupled to the electrode portions and comprising: at least one preprogrammed treatment program comprising at least one customizable treatment characteristic;

a stretch layer, wherein the electrode portions of the flexible circuit boards are mounted to either end of the stretch layer, wherein the control module is mounted on the stretch layer between the electrode portions wherein the stretch layer is configured to provide additional length or to take up any slack in accommodating various placement distances of the electrode portions, and wherein the extra length portions of the circuit boards are not mounted to the stretch layer;

a status indicator adapted to indicate at least one of a characteristic of the device and a characteristic of the preprogrammed treatment program;

a first control input configured to increase a level of the at least one customizable treatment characteristic and a second control input configured to decrease a level of the at least one customizable treatment characteristic, wherein the at least one treatment characteristic is customizable within a predetermined range, the first control input having a first set of tactile features, the second control input having a second set of tactile features, wherein the first set of tactile features comprises a different surface feature than the second set of tactile features, and wherein the first set of tactile features and the second set of tactile features are configured to enable a user to differentiate between the first control input and the second control input when the compact electrical stimulation device is positioned on an out-of-sight area of the user's body such that the user cannot utilize a visually-determined orientation of the compact electrical stimulation device to distinguish the first control input from the second control input; and a power source electrically coupled to the control module by the flexible cable.

22. The compact electrical stimulation device of claim 21, wherein the power source is integrated in the second electrode portion.

23. The compact electrical stimulation device of claim 21, wherein the power source is integrated in a connector coupled to the second end of the flexible cable.

24. The compact electrical stimulation device of claim 23, wherein the control module is disposable when the power source is depleted.

25. The compact electrical stimulation device of claim 21, wherein the at least one preprogrammed treatment program is selected from a group consisting of a transcutaneous electrical nerve stimulation (TENS) program, a muscle stimulation program, a massage program, a bone growth stimulation program, and a cartilage growth stimulation program.

26. The compact electrical stimulation device of claim 21, wherein the second end of the flexible cable comprises a strain relief connector coupled to the second electrode portion.

27. The compact electrical stimulation device of claim 21, wherein the control module comprises a snap connector selectively attachable to a corresponding snap connector of the first electrode portion.

28. The compact electrical stimulation device of claim 21, wherein the first set of tactile features comprises a different surface feature than the second set of tactile features.

29. The compact electrical stimulation device of claim 21, wherein one or more of the first and second sets of tactile features is a control button that is recessed or raised with respect to an outer housing or rim of the control module.

30. A compact electrical stimulation device comprising: a first and a second disposable and self-adhesive flexible circuit board comprising an electrode portion and an extra length portion;

a control module electrically coupled to the electrode portions and comprising: at least one preprogrammed treatment program comprising at least one customizable treatment characteristic;

a stretch layer, wherein the electrode portions of the flexible circuit boards are mounted to either end of the stretch layer, wherein the control module is mounted on the stretch layer between the electrode portions wherein the stretch layer is confilured to provide additional length or to take up any slack in accommodating various placement distances of the electrode portions, and wherein the extra length portions of the circuit boards are not mounted to the stretch layer;

status indicator means for indicating at least one of a characteristic of the device and a characteristic of the preprogrammed treatment program;

a first control input configured to increase a level of the at least one customizable treatment characteristic and second control input means configured to decrease a level of the at least one customizable treatment characteristic, wherein the at least one treatment characteristic is customizable within a predetermined range, the first control input means having a first contact area with a first set of tactile features, the second control input having a second contact area with a second set of tactile features, wherein the first set of tactile features comprises a different surface feature than the second set of tactile features, and wherein the first set of tactile features and the second set of tactile features are configured to enable a user to differentiate between the first control input and the second control input when the compact electrical stimulation device is positioned on an out-of-sight area of the user's body such that the user cannot utilize a visually-determined orientation of the compact electrical stimulation device to distinguish the first control input from the second control input; and power supply means.

31. The compact electrical stimulation device of claim 30, wherein one or more of the first and second sets of tactile features is a control button that is recessed or raised with respect to an outer housing or rim of the control module.

\* \* \* \* \*

UNITED STATES PATENT AND TRADEMARK OFFICE
CERTIFICATE OF CORRECTION

Page 1 of 1

PATENT NO. : 8,958,883 B2
APPLICATION NO. : 11/918761
DATED : February 17, 2015
INVENTOR(S) : Pierre-Yves Mueller It is certified that error appears in the above-identified patent and that said Letters Patent is hereby corrected as shown below:

Specification

In column 11 at line 21, Change "semitransparent" to --semi-transparent--.

Claims

In column 14 at line 56, In Claim 1, change "portions" to --portions,--.

In column 16 at line 15, In Claim 15, change "portions" to --portions,--.

In column 17 at line 8 (approx.), In Claim 21, change "portions" to --portions,--.

In column 18 at line 22, In Claim 30, change "portions" to --portions,--.

In column 18 at line 23, In Claim 30, change "confilured" to --configured--.

Signed and Sealed this
Tenth Day of November, 2015

Michelle K. Lee
*Director of the United States Patent and Trademark Office*